United States Patent [19]
Genga et al.

[11] Patent Number: 5,810,001
[45] Date of Patent: Sep. 22, 1998

[54] ANESTHETIC TRANSFER SYSTEM

[75] Inventors: Rodolfo Genga, Rome; Pierantonio Salvador, Udine, both of Italy

[73] Assignee: Abbott Laboratories, Abbott Park, Ill.

[21] Appl. No.: 696,980

[22] PCT Filed: Jan. 4, 1995

[86] PCT No.: PCT/US95/00203

§ 371 Date: Jun. 12, 1996

§ 102(e) Date: Jun. 12, 1996

[87] PCT Pub. No.: WO95/18644

PCT Pub. Date: Jul. 13, 1995

[30] Foreign Application Priority Data

Jan. 7, 1994 [IT] Italy .................................. M194A0009

[51] Int. Cl.⁶ ............................ A62B 9/04; A61M 15/00; A61M 16/10

[52] U.S. Cl. ................................ 128/202.27; 128/203.12; 128/203.21

[58] Field of Search ................. 128/202.27, 203.12, 128/203.21

[56] References Cited

U.S. PATENT DOCUMENTS

| | | | |
|---|---|---|---|
| 3,938,520 | 2/1976 | Scislowicz et al. | 128/202.27 |
| 4,132,334 | 1/1979 | Danks | 128/202.27 |
| 4,351,327 | 9/1982 | Rinne et al. | 128/200.14 |
| 4,867,212 | 9/1989 | Mohr et al. | 128/200.14 |
| 4,883,049 | 11/1989 | McDonald | 128/202.22 |
| 4,932,398 | 6/1990 | Lancaster et al. | 128/200.14 |
| 5,144,984 | 9/1992 | Westerberg et al. | 128/202.27 |
| 5,293,865 | 3/1994 | Altner et al. | 128/202.22 |

FOREIGN PATENT DOCUMENTS

| | | | |
|---|---|---|---|
| 0448954 | 2/1991 | European Pat. Off. | 128/202.27 |
| 0455433 | 11/1991 | European Pat. Off. | 128/202.27 |
| 855535 | 12/1960 | United Kingdom | 128/202.27 |
| 884078 | 12/1961 | United Kingdom | 128/202.27 |
| 1555267 | 11/1979 | United Kingdom | 128/202.27 |
| 2252962 | 8/1992 | United Kingdom | 128/202.27 |
| 9212752 | 8/1992 | WIPO | 128/202.27 |
| 9212753 | 8/1992 | WIPO | 128/202.27 |

*Primary Examiner*—Kimberly L. Asher
*Attorney, Agent, or Firm*—Neal D. Marcus; Brian R. Woodworth

[57] ABSTRACT

A system and apparatus are provided for connecting an anesthetic container (14) to a vaporizer. Indicia are provided on the container (14) or on a transfer tube (12) connected to the container (14) and the indicia can include mechanical keys, electrical keys and electronic keys. A transfer device is provided for mounting to the vaporizer and engaging the container (14) or transfer tube (12) connected to the container (14). The transfer device includes a sensing system such as a key or code reader system. A clamping mechanism is provided for clamping the container (14), or end pin (16) of a transfer tube (12) connected to the container (14), in a leak-tight engagement within the transfer device. The transfer device can accommodate movement between a fill position and a drain position. The internal fluid flow passages are blocked except when the transfer device is in the fill or drain position.

16 Claims, 17 Drawing Sheets

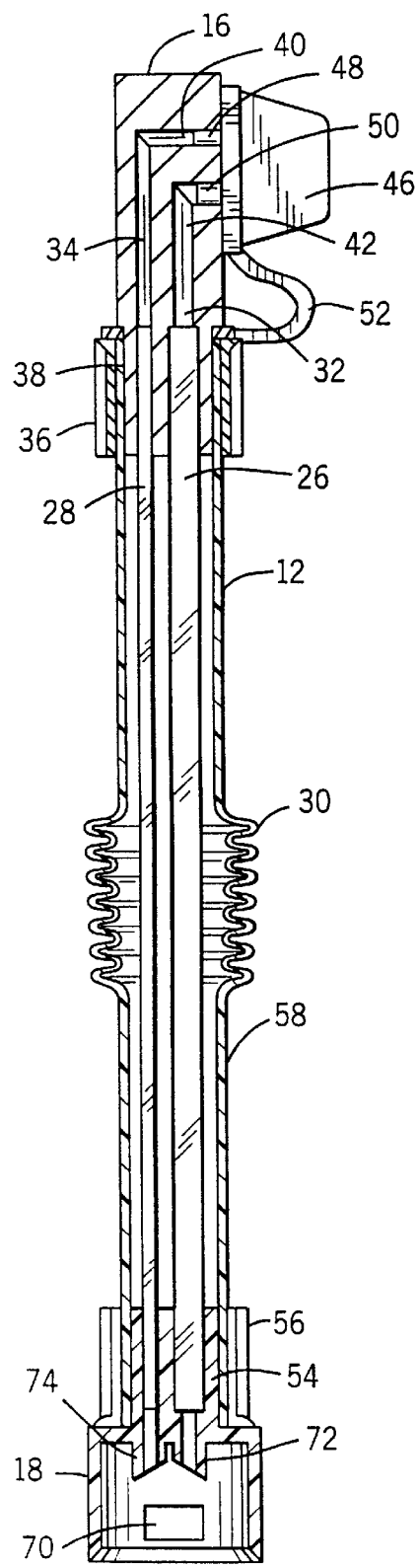
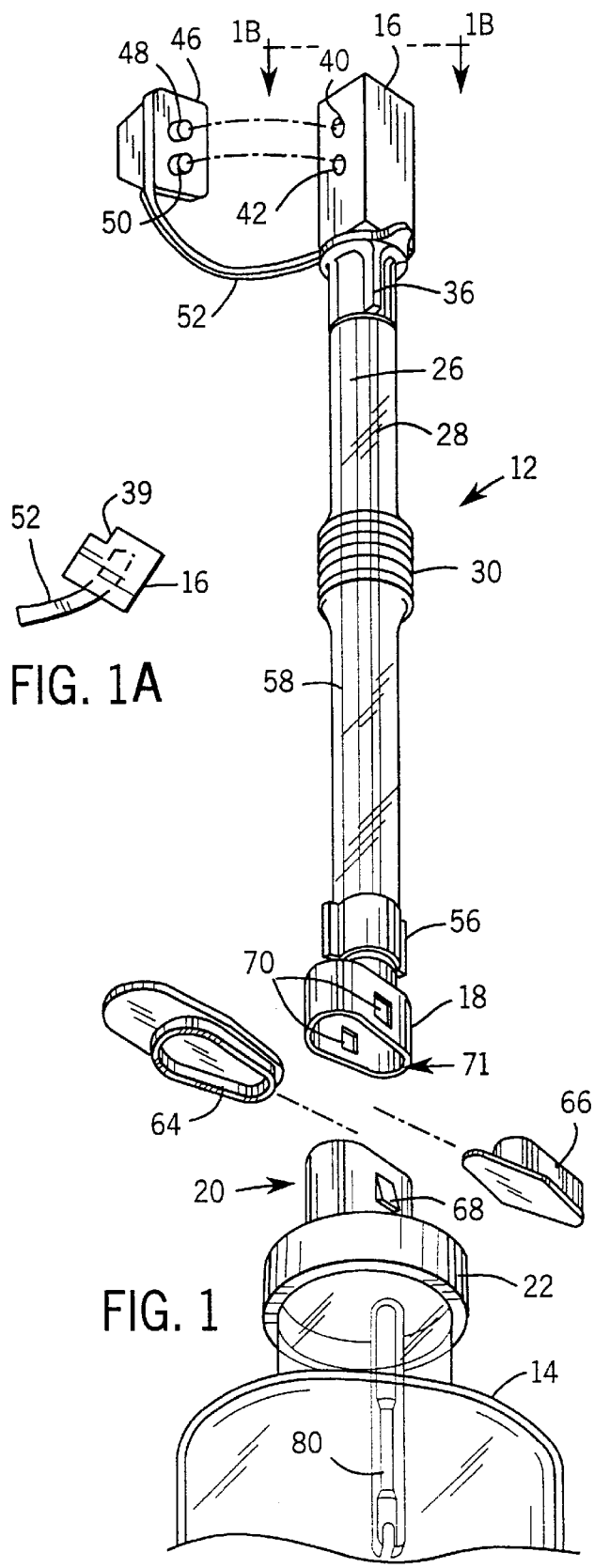
FIG. 1A
FIG. 1
FIG. 2

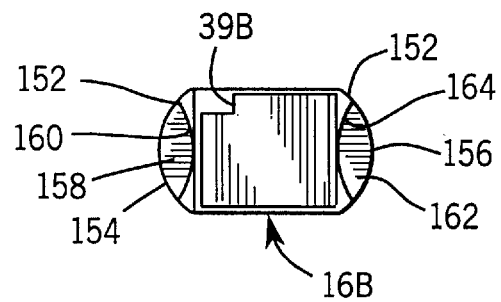
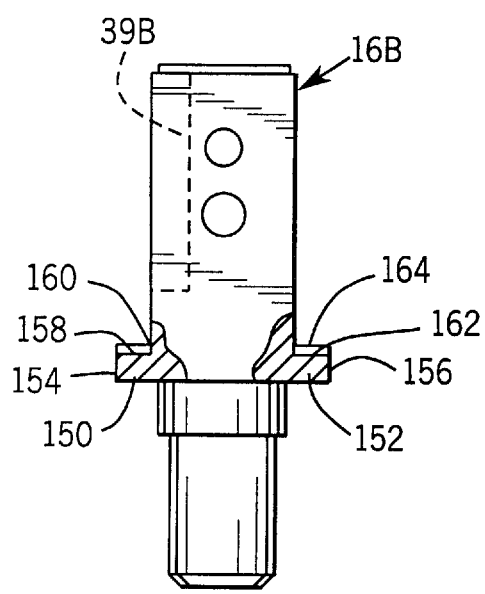
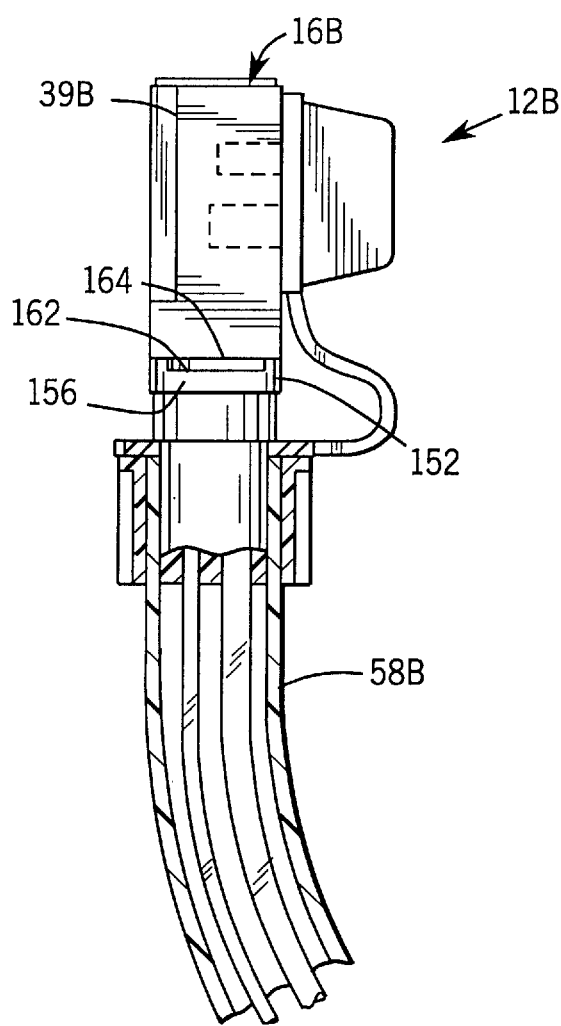

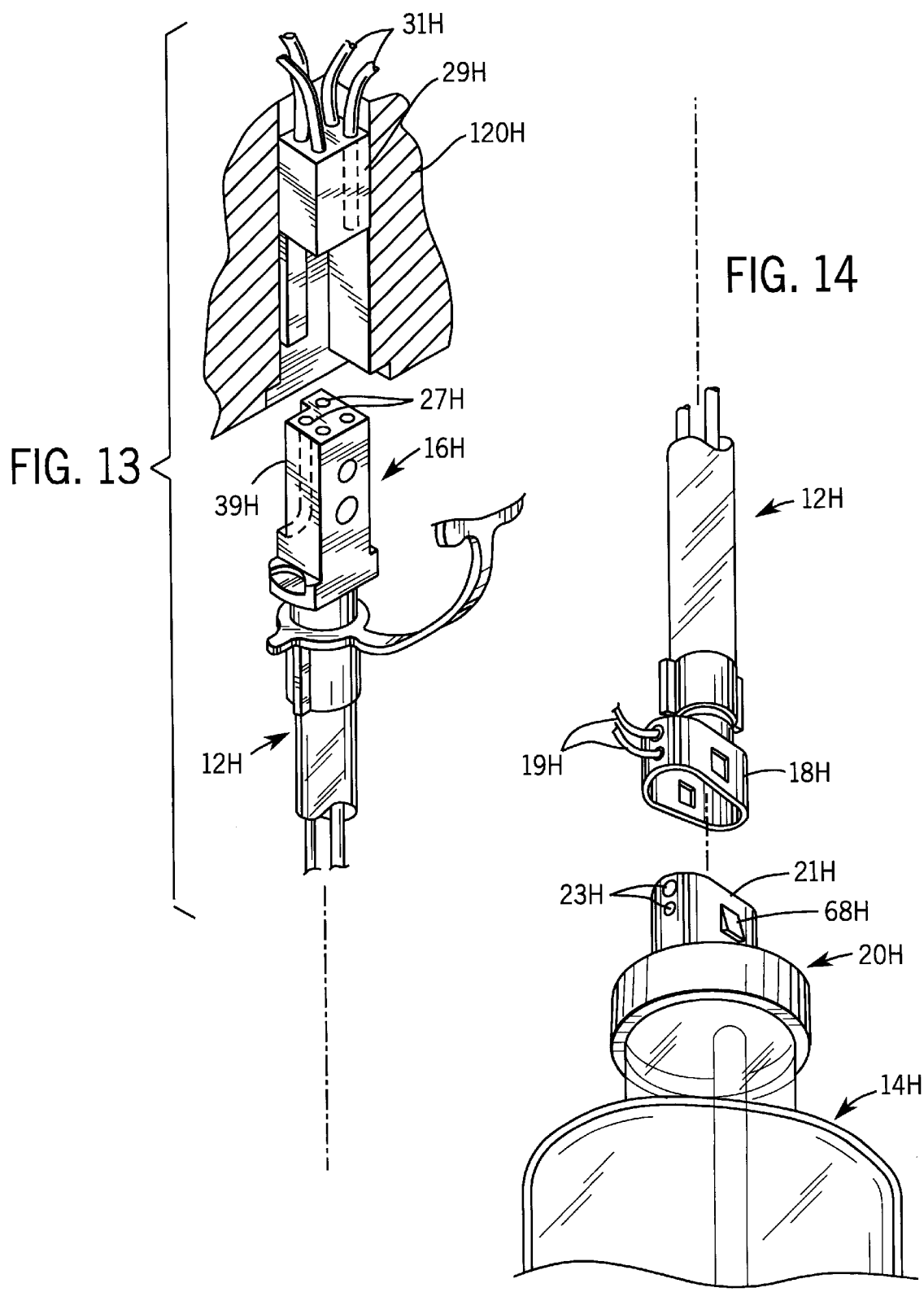

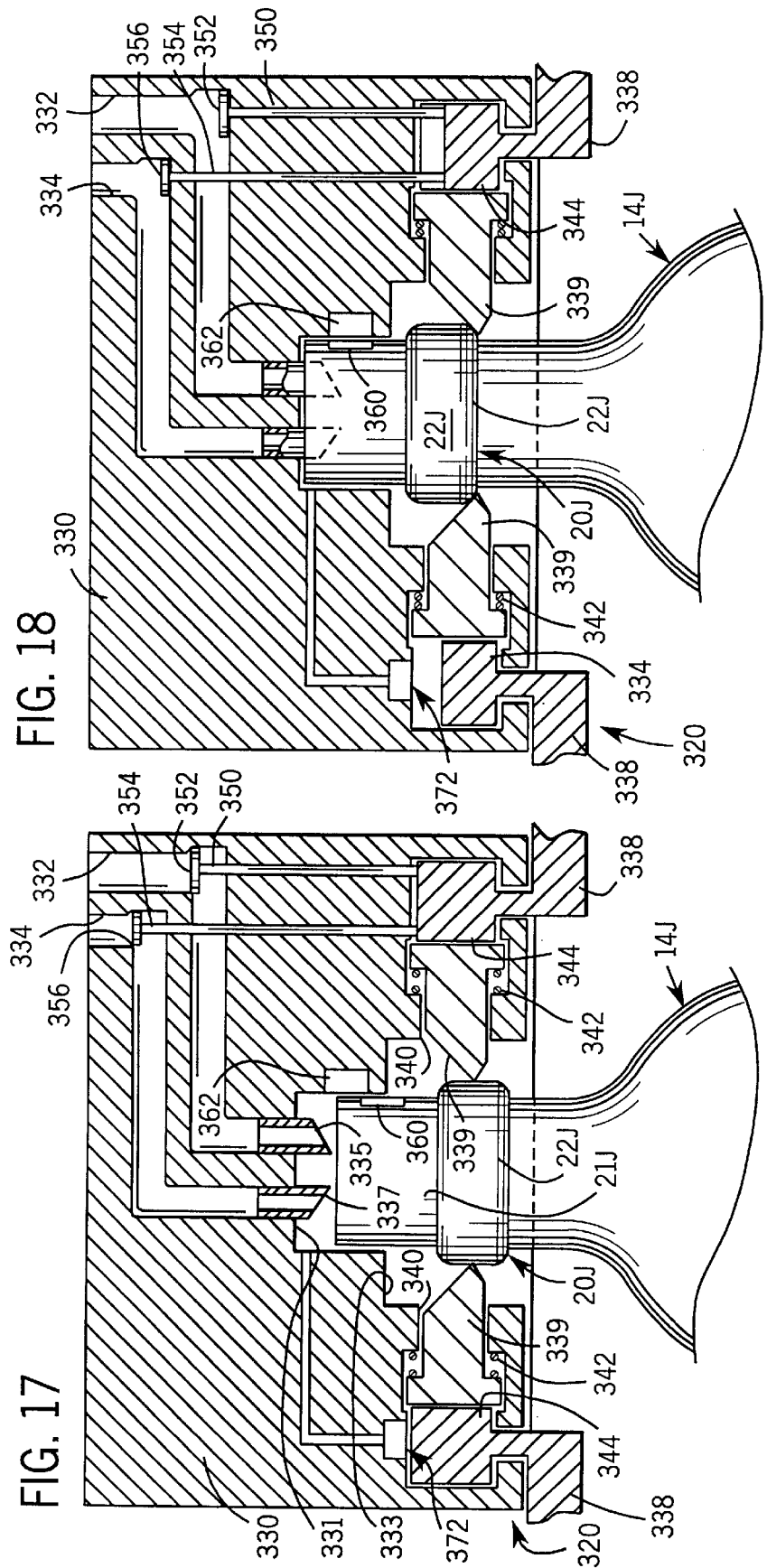

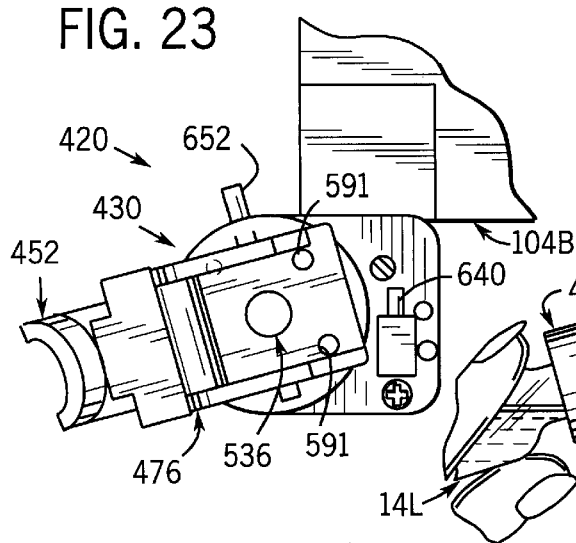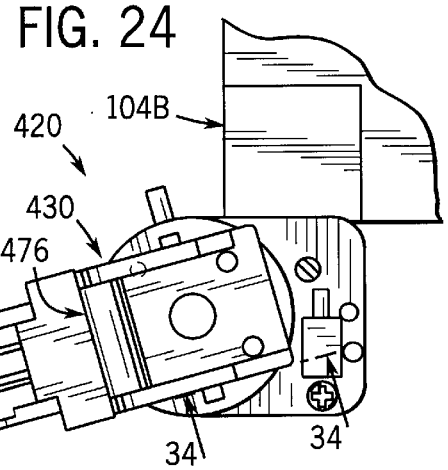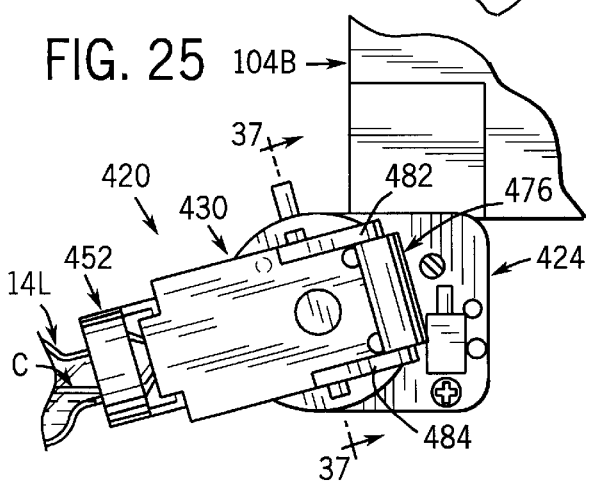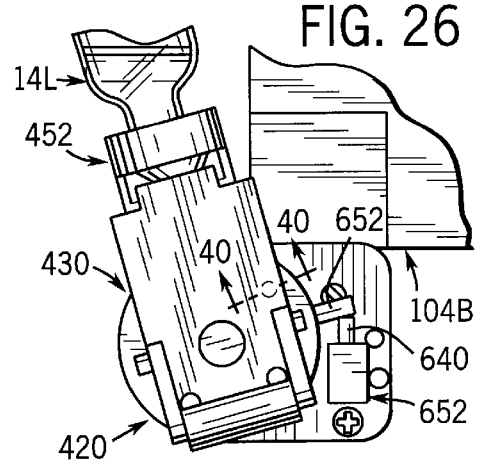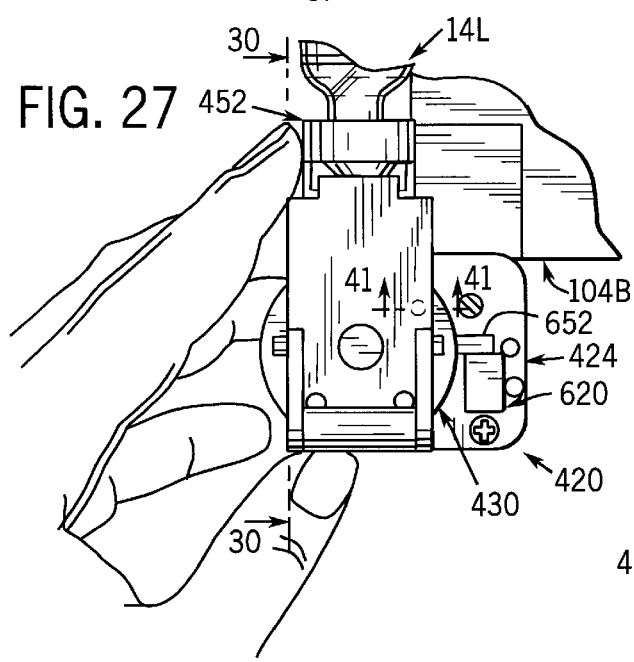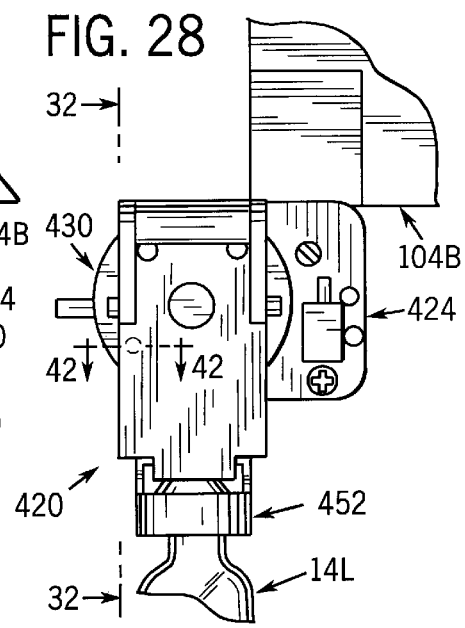

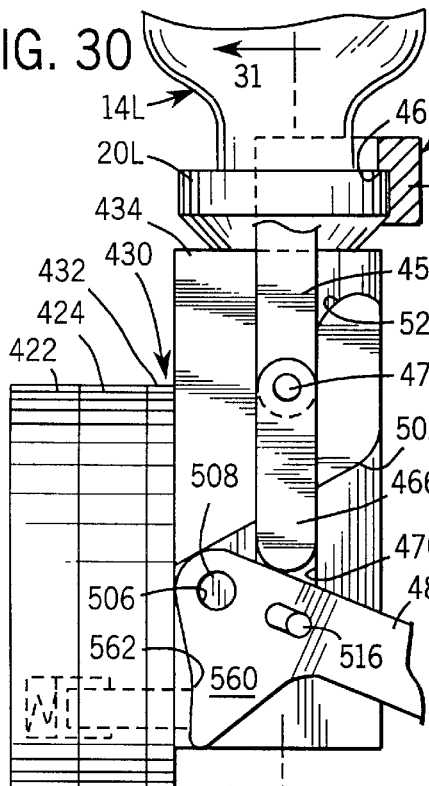
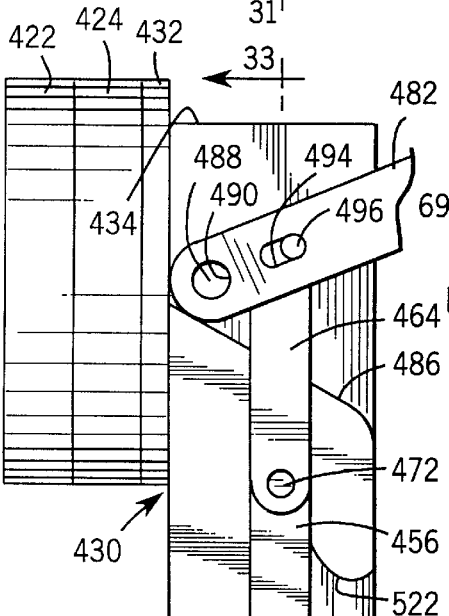
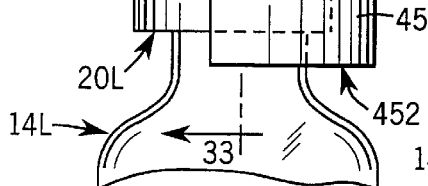
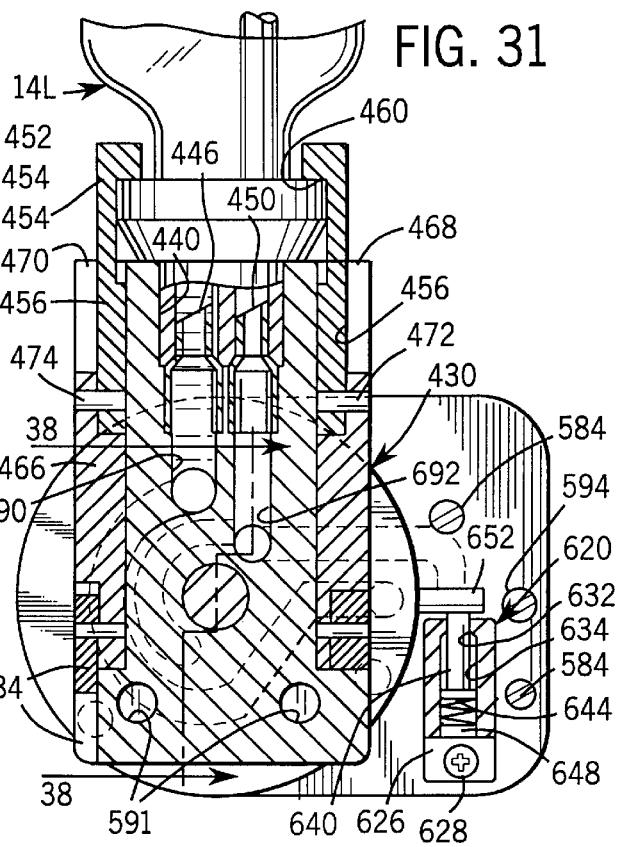
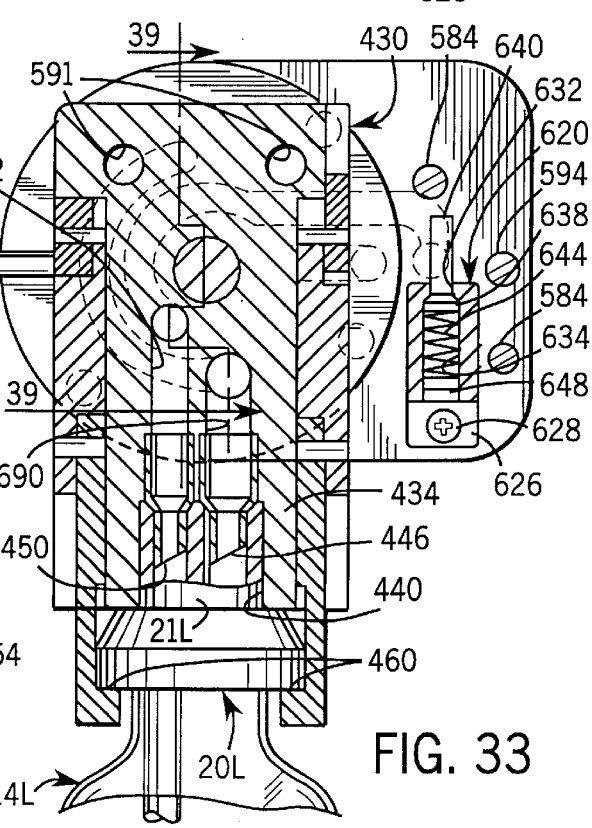

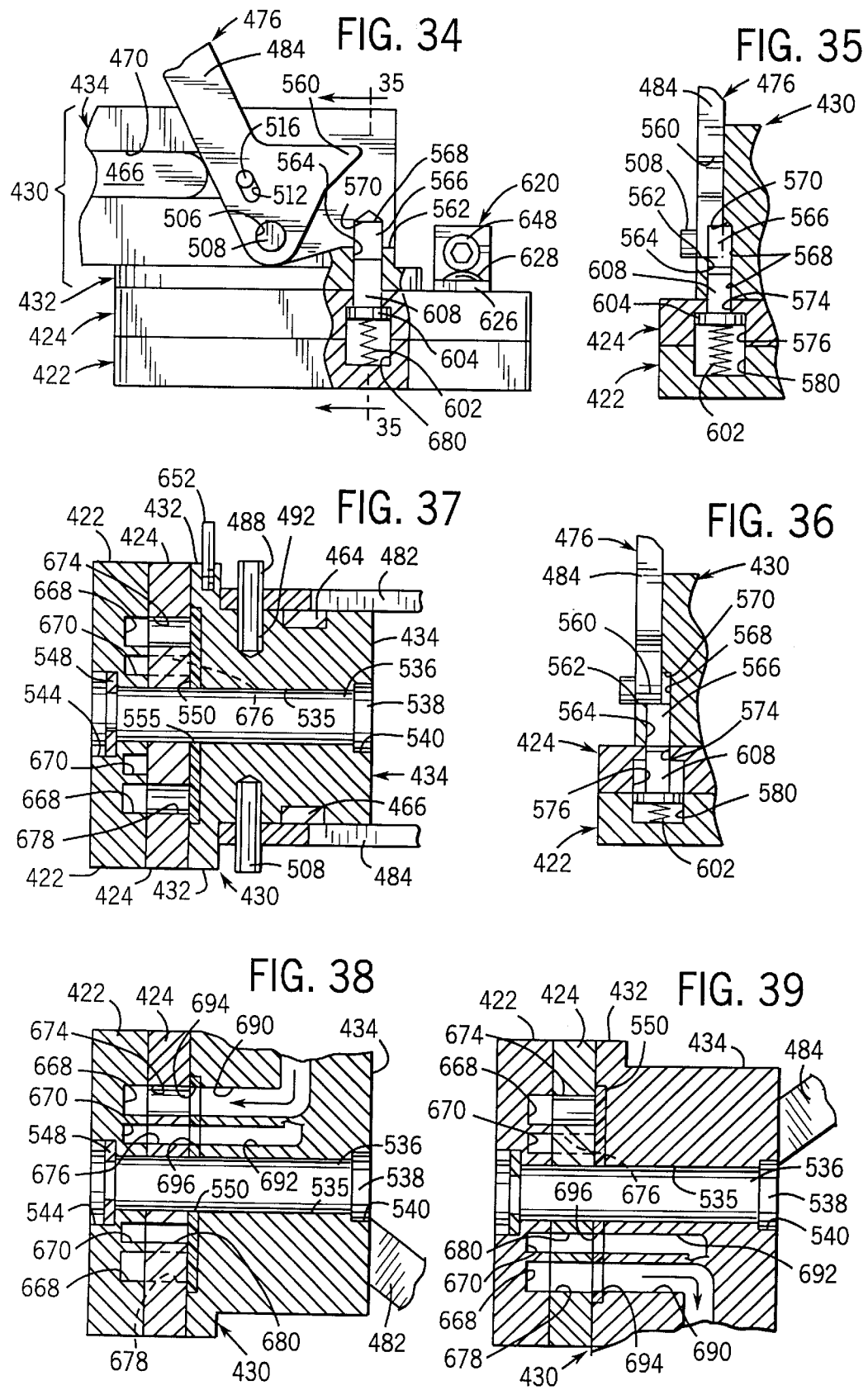

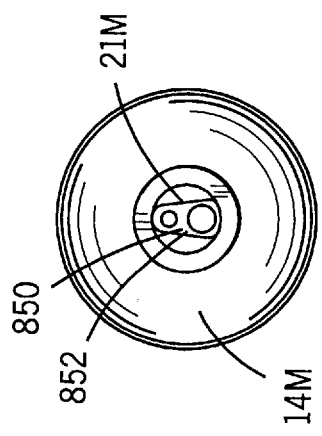
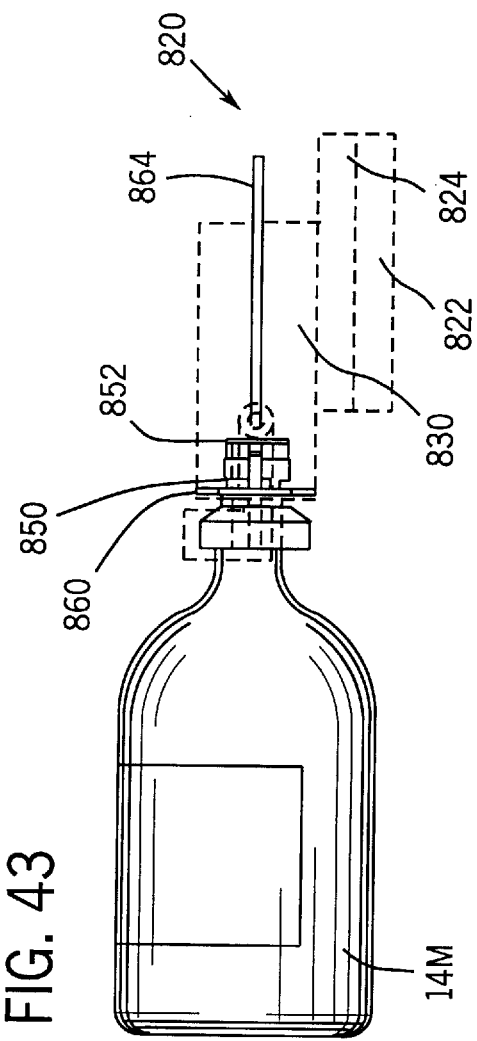
FIG. 48
FIG. 47
FIG. 43
FIG. 44
FIG. 45
FIG. 46

ANESTHETIC TRANSFER SYSTEM

This application is a 371 of PCT/US95/00203 filed Jan. 4, 1995.

TECHNICAL FIELD

The present invention relates to a system for use in medical facility operating rooms to safely accommodate the transfer of an anesthetic from a container to administration equipment, such as a vaporizer.

BACKGROUND OF THE INVENTION AND TECHNICAL PROBLEMS POSED BY THE PRIOR ART

Inhalable anesthetics are typically volatile substances with relatively low boiling points and high vapor pressures. They can be flammable and explosive substances in both their liquid and vapor states. Further, inhalation of the vapor by health care personnel can cause drowsiness.

Therefore, such anesthetics must be safely handled in operating rooms in order to minimize the risk of inhalation by medical personnel as well as to minimize the risk of fire or explosion. Preferably, the anesthetic should be used in a way which will ensure that there is little or no release to the atmosphere at all stages of handling during normal surgical procedures.

Anesthetics are typically dispensed in liquid form to an apparatus, such as an anesthetic vaporizer, which mixes the anesthetic with oxygen and nitrous oxide. The mixture is supplied in gaseous form to the patient for inhalation.

Devices have been designed for the transfer of an anesthetic from a supply container to a vaporizer through a closed system that eliminates the escape of an anesthetic gas to the atmosphere. The devices are designed so that during set-up and disassembly procedures, a supply container of anesthetic is not open and exposed to the atmosphere in the operating room.

One system which has been developed for connecting an anesthetic container to a vaporizer is the SECURITY LOCK™ Vapofill vaporizer connector sold by Abbott Laboratories, Inc., One Abbott Park Road, Abbott Park, Ill. 60064-3500, U.S.A. and Abbott S.p.A., 04010 Campoverde, Latina, Italia. It may be disposable, and it employs a connector tube having special connecting or coupling members at both ends. The tube is flexible and is kink-resistant. The vaporizer end of the tube is provided with a vaporizer connector, adaptor, coupling member, or pin that engages an anesthetic vaporizer. This can be initially closed with a removable cap. The end of the tube attached to the anesthetic container is provided with a closure adaptor that engages a closure on the anesthetic container.

The closure is preferably connected to the anesthetic container prior to use in the operating room. The container closure has a frangible seal adapted to be perforated by a piercing means within the closure adaptor as the adaptor engages the closure. Following perforation of the frangible seal by the piercing means, the closure adaptor and closure remain locked together, and this permits the transport of anesthetic through the tube from the supply container to the vaporizer. The system remains closed to the atmosphere throughout the assembly or disassembly procedures.

Some types of vaporizers are intended for use with only a specific anesthetic or anesthetics. In such situations, care must be taken to insure that only the proper anesthetic is dispensed into the particular vaporizer. To this end, the above-discussed SECURITY LOCK™ device has been provided with a keying system to prevent the use of the device with an anesthetic for which it is not designed.

In particular, the anesthetic container closure has a specific shape, and the connector tube closure adaptor has a complementary shape for mating with the container closure. At the other end of the container tube, the pin has a special shape for mating with a complementary portion of the vaporizer anesthetic inlet port.

Vaporizer manufacturers provide standard inlet port configurations. These are standardized to I.S.O. ("International Standardization Organization") configurations specific to various types of anesthetics. Because the container for each type of anesthetic has its own special closure shape, and because the corresponding connector device fits only the type of vaporizer designed for that type of anesthetic, the probability of inadvertently using the wrong type of anesthetic in a vaporizer is greatly reduced.

Although such keyed, connector tubes function satisfactorily, there are inventory, installation, operation, and management requirements and considerations associated with their proper use. It would be desirable to minimize such requirements and considerations.

While the use of a SECURITY LOCK™ transfer device is effective in forming a leak-tight seal at the vaporizer when properly installed, it would be desirable to provide a system with improved connection structures or engagement structures for minimizing the likelihood that the transfer device can be improperly connected at the vaporizer. Such an improved system should facilitate the formation of a connection that is not susceptible to leakage of the anesthetic liquid or vapor.

Preferably, such a system should have the capability for including, where desired, a means for preventing transfer of the anesthetic and/or operation of the vaporizer unless a proper, leak-tight connection is made at the vaporizer.

In addition, the inventors of the present invention have discovered that it would be useful to provide other features in an improved transfer system. Specifically, it would be advantageous to provide such a transfer system with improved means for inhibiting use (misuse) of a vaporizer with any agent other than a specific anesthetic in a particular type of container designed for the vaporizer. Such an improved transfer system should desirably also be resistant to intentional misuse or tampering.

A further benefit of such a system would be the capability to provide warning and/or status indications or alarms. For example, it would be desirable to provide an indication that the connection has been properly made and an indication that the correct anesthetic container and vaporizer have been connected.

It may also be beneficial in some cases to provide such an improved system with the capability for incorporating a control system for setting, or interlocking with, the operational system of the vaporizer. For example, it may be advantageous in some applications to incorporate a control system for controlling the operation of the vaporizer only when the vaporizer is connected to a predetermined type of container of a specific anesthetic.

Alternatively, such a control system might have the capability for accommodating a plurality of different anesthetics. Such systems may advantageously include coding and code reading features to function with an essentially automatic control system for operation of the vaporizer depending on the type of anesthetic detected by the code reading feature. Such automatic control might, in some cases, be advantageously extended to other anesthesia equipment, such as the fresh gas mixer, the respirator, the scavenging systems, etc.

Further, it would be beneficial if such an improved system could, where desired, document or record the connection parameters and operational conditions while the anesthetic container is connected to the vaporizer, and optionally, also before and after the connection is made at the vaporizer.

Advantageously, such an improved system could include means for recognizing and recording codes corresponding to the type of anesthetic, the container size, and the expiration date. In some situations, it would be desirable to interlock the means for identifying such parameters with the vaporizer control system to prevent operation of the vaporizer whenever the identified parameters do not match a predetermined set of parameters stored or set in the control system.

The present invention provides an improved anesthetic transfer system which can accommodate designs having the above discussed benefits and features.

SUMMARY OF THE INVENTION

One aspect of the invention includes a process for facilitating the proper transfer of anesthetic from a container to a vaporizer. The process includes the steps of providing the container with at least one indicium and connecting the container to the vaporizer. The indicium is sensed when the container is properly connected to the vaporizer. A signal is generated responsive to the sensing of the indicium upon establishment of the connection.

In a preferred embodiment, at least one indicium is provided to identify a system characteristic, such as container size, anesthetic type, expiration date and/or proper position of the container. Indicia can be provided in a code as a predetermined set of data or information in a number of forms: a structural key configurations, electrical contacts, electronic data-storage media including surface acoustic wave devices and a magnetic-storage media, and optically readable surface indicia, such as a laser scannable bar code record or an optical color system.

According to another aspect of the invention, the process for facilitating proper transfer of anesthetic from a container to a vaporizer includes providing a transfer tube with at least one indicium. One end of the transfer tube is connected to the vaporizer and the other end of the tube is connected to the container. The indicium is sensed when the container is connected via the tube to the vaporizer, and a signal is generated responsive to the sensing of the indicium upon the establishment of the connection.

In one form of the process, at least one indicium is provided on the container which is connected to the vaporizer with a transfer tube. The tube includes a sensing system located at the region where the container is connected to the tube, and the sensing system senses the indicium on the container. Also, indicia can be provided on the end of the tube connected to the vaporizer instead of, or in addition to, indicia on the container. Such indicia is sensed by a sensing system which can be incorporated at the vaporizer connection or other transfer device on or in the vaporizer.

According to another aspect of the invention, the above-described processes can be effected with apparatus which includes a sensor on a transfer device portion (connection assembly) of the vaporizer for sensing the indicium on the container or connector tube. A signal generator is provided for generating a signal responsive to the sensing of the indicium. A tube may be employed to connect the container to the vaporizer, and if an indicium is provided on the container in such a case, the mating end of the connector tube includes a sensor for sensing the indicium.

Another aspect of the invention relates to an improved coupling member for one end of a connector tube assembly or transfer tube wherein the coupling member has a first anesthetic-specific key configuration identifying a specific anesthetic and is connectible to a specific anesthetic vaporizer. The other end of the transfer tube is connectible to a container of anesthetic for facilitating the proper transfer of anesthetic from the container to the vaporizer. At least one indicium can be included on the coupling member to provide information in addition to the specific anesthetic identification provided by the first key configuration.

Yet another aspect of the invention relates to an improved coupling member or pin for one end of a connector tube or assembly which is connectible to a transfer device on an anesthetic vaporizer and wherein the other end of the tube is connectible to an anesthetic container. The coupling member includes an end pin for being connected to the vaporizer. At least one flange extends outwardly from the pin to engage the transfer device and to define at least one indicium that (1) is indicative of a predetermined characteristic and (2) can be sensed by the transfer device.

Another aspect of the invention also relates to an improved coupling member or pin for one end of a connector tube or assembly which is connectible to a transfer device on an anesthetic vaporizer and wherein the other end of the tube is connectible to a anesthetic container. At least one indicium is located on the coupling member. The indicium is indicative of a predetermined characteristic, and the indicium includes at least one of the following: an electrical conductor contact configuration; a surface acoustic wave device, magnetic data-storage medium, or other electronic data-storage medium; and an optically readable surface indicium.

In another form of the invention, a device is provided for receiving a coupling member of a connector tube assembly connectible to an anesthetic container wherein the coupling member defines at least one anesthetic discharge passage. The device includes a body defining (1) a receiving cavity for the coupling member, (2) a fixed cam surface, and (3) at least one fluid transfer passage extending from the receiving cavity through the body. The device also includes a rotatable member mounted for rotation on the body. The rotatable member defines a rotatable cam surface. A clamp member is disposed in the body adjacent the receiving cavity. The clamp member has a first cam follower surface adjacent the fixed cam surface and has a second cam follower surface adjacent the rotatable cam surface. Rotation of the rotatable member drives the clamp member against the coupling member to clamp the coupling member within the body with communication established within the discharge passage and the transfer passage.

Yet another aspect of the invention relates to a fluid transfer device for receiving a pierceable closure on an anesthetic container. The device includes a body defining (1) a receiving port for the container closure, (2) a piercing conduit extending into the port, (3) a recess, and (4) at least one fluid transfer passage extending from the piercing conduit through the body. A rotatable member is mounted for rotation on the body and defines a rotatable cam surface. A clamp member is disposed in the body recess adjacent the receiving cavity. The clamp member has a first cam follower surface adjacent the rotatable cam surface and has an inwardly movable cam surface. Rotation of the rotatable member drives the clamp member against the container closure to (1) urge the container closure further into the receiving port wherein the closure is pierced by the piercing conduit and (2) clamp the pierced closure in a fixed position.

In another form of the invention, a transfer device is provided for mounting on an anesthetic vaporizer for connecting the vaporizer with a container of liquid anesthetic. The transfer device includes a first body adapted to be attached to the vaporizer. The body defines (1) a receiving bore, (2) a fluid transfer passage extending from the vaporizer to communicate with at least two locations on an inside circumference of the bore. The device also includes a second body. The second body defines a port for communicating with the container and defines a cylindrical portion received in the bore for accommodating (1) rotation of the second body about an axis relative to the first body and (2) movement of the second body cylindrical portion axially along the bore. The cylindrical portion defines a fluid transfer passage extending from the port to the bore. The second body can be moved axially between (1) a first axial position blocking flow between the first and second bodies and (2) a second axial position permitting flow between the first and second bodies in at least two different rotated positions of the second body.

Another embodiment of the transfer device, which is suitable for mounting on an anesthetic vaporizer to connect the vaporizer with a container of liquid anesthetic, also includes a first body adapted to be attached to the vaporizer. The body defines (1) a receiving bore and (2) a fluid transfer passage extending from the vaporizer to communicate with the inside of the bore. A second body includes a port for communicating with the container and a cylindrical portion received in the bore for accommodating (1) rotation of the second body about an axis relative to the first body and (2) movement of the second body cylindrical portion axially along the bore. The cylindrical portion defines a fluid transfer passage extending from the port to at least two locations on an inside circumference of the bore. The second body can be moved axially between (1) a first axial position blocking flow between the first and second bodies and (2) a second axial position permitting flow between the first and second bodies in at least two different rotated positions of the second body.

According to another aspect of the invention, a transfer device is provided for mounting on an anesthetic vaporizer to connect the vaporizer with an anesthetic container having a pierceable closure. The transfer device includes a body defining a region for receiving the closure. At least one hollow piercing spike is provided at the receiving region for piercing the closure. The body defines a passage between the spike and the vaporizer. A clamp is adapted to engage the closure and is movable between an extended position and a retracted position. An operating handle is connected to the clamp for moving the clamp between the extended and retracted positions whereby the container closure is urged against the spike which pierces the closure and whereby the container closure is clamped against the body.

Another form of a transfer device is provided for mounting on an anesthetic vaporizer for connecting a fluid passage of the vaporizer with an anesthetic container. This device includes a stationary portion and a rotatable body mounted for rotation on the stationary portion. The stationary portion has a fluid passage communicating between the vaporizer fluid passage and at least two locations on a circular arc. The body defines a receiving region to which the container can be connected. The body also defines a fluid passage communicating between the container and the stationary portion fluid passage when the body is in each of two rotated positions. One of the positions is a fill position and the other position is a drain position.

In a preferred embodiment, the stationary portion and rotatable body define generally flat, mating faces. The stationary portion defines a fluid passage communicating between the vaporizer fluid passage and the face of the stationary portion. The rotatable body defines a fluid passage communicating between the container and the face of the rotatable body. The fluid passages of the stationary portion and rotatable body are in communication only in two rotated positions of the rotatable body.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same, FIG. 1 is an exploded, fragmentary, perspective view of an anesthetic container and a connector tube for attaching the anesthetic container to a prior art vaporizer (not illustrated);

FIG. 1A is a fragmentary, top plan view of the connector tube taken generally along the plane 1B—1B in FIG. 1;

FIG. 2 is a cross-sectional view of the connector tube shown in FIG. 1;

FIG. 5 is a fragmentary, side elevational view, partially in cross-section, of one end of an anesthetic transfer system connector tube having an end pin which is adapted to be received in a vaporizer or intermediate transfer device connected to a vaporizer;

FIG. 6 is a front elevational view of the end pin illustrated in FIG. 5 with the connector tube omitted for ease of illustration;

FIG. 7 is a top, plan view of the end pin illustrated in FIG. 6;

FIG. 13 is a fragmentary, exploded, perspective view of another embodiment of a connector tube end pin and of a portion of a vaporizer adapted to mate with it;

FIG. 14 is a fragmentary, exploded, perspective view of a container and a mating end of another embodiment of a connector tube;

FIGS. 17 and 18 are simplified, partially diagrammatic, cross-sectional views of other forms of transfer devices and an anesthetic container;

FIGS. 23–28 are front elevational views of the transfer device shown in FIGS. 21 and 22, and FIGS. 23–28 show the sequence of operation of the transfer device;

FIG. 30 is an enlarged, fragmentary, cross-sectional view of a portion of the transfer device taken along the plane 30—30 in FIG. 27 and showing the load/unload, "home" position of the device with the latch pin in an unlatched condition;

FIG. 31 is a cross-sectional view taken generally along the plane 31—31 in FIG. 30;

FIG. 32 is a side elevational view taken generally along the plane 32—32 in FIG. 28;

FIG. 33 is a cross-sectional view taken generally along the plane 33—33 in FIG. 32;

FIG. 34 is an enlarged, fragmentary side elevational view taken generally along the plane 34—34 in FIG. 24;

FIG. 35 is a fragmentary, cross-sectional view taken generally along the plane 35—35 in FIG. 34;

FIG. 36 is a view similar to FIG. 35, but FIG. 36 shows the latch pin disengaged when the operating handle is moved rearwardly;

FIG. 37 is a fragmentary, cross-sectional view taken generally along the plane 37—37 in FIG. 25;

FIG. 38 is a fragmentary, cross-sectional view taken generally along the plane 38—38 in FIG. 31;

FIG. 39 is a fragmentary, cross-sectional view taken generally along the plane 39—39 in FIG. 33;

FIG. 43 is a simplified, diagrammatic, side elevational view of an anesthetic container received in a transfer device which can be mounted to a vaporizer;

FIG. 44 is a side elevational view of a microprocessor chip and colored element which are incorporated in the container illustrated in FIG. 43;

FIG. 45 is a top, plan view of the element shown in FIG. 44;

FIG. 46 is an end view of the closure on the container shown in FIG. 43 wherein the closure includes the microprocessor chip and colored element illustrated in FIGS. 44 and 45;

FIG. 47 is a front view of an annular antenna which is mounted in the transfer device illustrated in FIG. 43; and FIG. 48 is a side elevational view of the antenna shown in FIG. 47.

DESCRIPTION OF THE PREFERRED EMBODIMENTS

Figure 3:
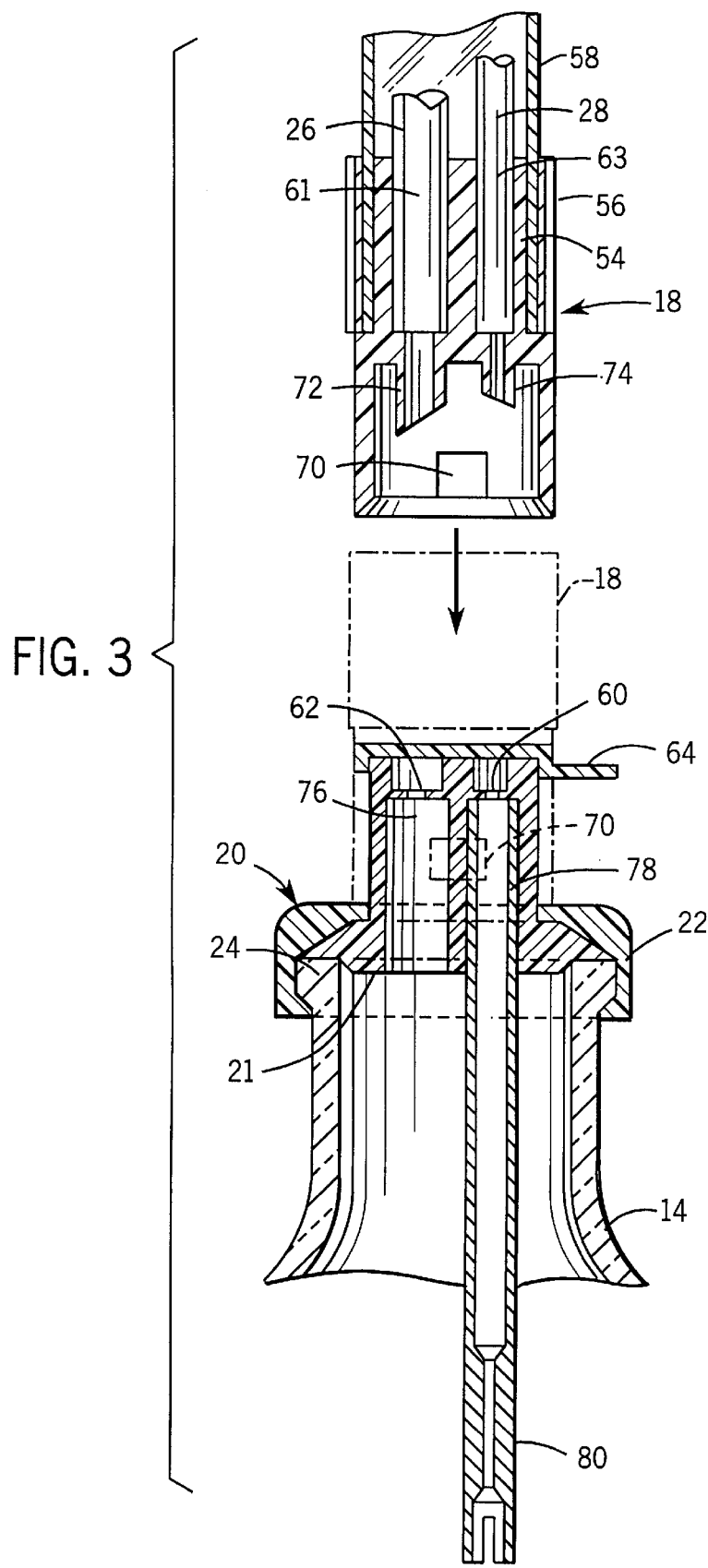
FIG. 3 is a greatly enlarged, fragmentary, cross-sectional view of an end of the connector tube and container shown in FIG. 1.

The present invention provides a novel system which includes processes and apparatus for connecting an anesthetic container to a vaporizer. The system can be provided in a number of different designs incorporating a variety of different features and capabilities.

According to one aspect of the invention, the transfer device includes means for connecting the anesthetic container to the vaporizer with improved holding or engaging structures.

Another aspect of the invention includes novel processes for reading, using, and recording the design and operational data or conditions. This can be used in monitoring, interlocking, controlling, and operating transfer devices and anesthesia equipment.

The processes can be effected with code reader systems and unique coding systems incorporating indicia, including mechanical keys, electrical keys, electronic keys, associated detectors, monitoring and warning systems, recording systems, operating systems, and control systems.

Yet another aspect of the invention includes multiposition transfer devices with internal valve systems permitting the dispensing of an anesthetic from a container to the vaporizer and permitting draining of anesthetic from the vaporizer back into the container. The transfer devices can be provided with mechanisms for actuating the valves only if the container is properly connected.

Various apparatus of some of the invention systems can be provided in a modular format. Insert parts can be provided to accommodate a variety of different containers and vaporizers with a single, main transfer mechanism.

While this invention is susceptible of embodiment in many different forms, this specification and the accompanying drawings disclose only some specific forms as examples of the invention. The invention is not intended to be limited to the embodiments so described, however. The scope of the invention is pointed out in the appended claims.

For ease of description, the system components of this invention are described in the normal operating position, and terms such as upper, lower, horizontal, etc., are used with reference to this position. It will be understood, however, that the components of this invention may be manufactured, stored, transported, and sold in an orientation other than the position described.

Figures illustrating the components of the invention show some mechanical, electrical, and electronic elements that are known and that will be recognized by one skilled in the art. The detailed descriptions of such elements are not necessary to an understanding of the invention and, accordingly, are herein presented only to the degree necessary to facilitate an understanding of the novel features of the present invention.

FIG. 1 shows a prior art system for filling a conventional anesthetic vaporizer (not shown) by using a transfer device that includes a connector tube or tube assembly 12 and an anesthetic supply container 14. The tube assembly 12 includes a connector member 16 (which can be alternatively designated as a coupling member, vaporizer adaptor, or end pin) for connecting the tube assembly 12 to the vaporizer. The other end of the tube assembly 12 includes a closure adaptor 18. This system is marketed by Abbott Laboratories, Inc., One Abbott Park Road, Abbott Park, Ill. 60064-3500, U.S.A. and by Abbott S.p.A., 04010 Campoverde, Latina, Italia under the trademark SECURITY LOCK Vapofill.

As shown in more detail in FIG. 3, the closure 20 is mounted on the supply container 14 with a collar 22 retaining the closure 20 on the container 14. The collar 22 is designed to snap-fit over the upper flange 24 of container 14. Alternatively, the closure 20 can be retained on the container 14 by a metal crimp (not shown). A lower portion 21 of the closure 20 seats within the open neck of the container 14. Downward pressure from the collar 22 effectively seals the contents of the supply container 14 from the atmosphere.

As best shown in FIG. 2, the connector tube 12 houses two tubes which are designed to connect the container 14 to the vaporizer. In the embodiment shown, these are (1) a filling member, tube, or conduit 26 which defines a discharge passage and (2) a venting member, tube, or conduit 28 which defines a gas vent passage, both positioned internally to the cover member 58. (In an alternative design, the cover member 58 could function as either the filling conduit or the venting conduit, in which case there would be only one conduit within the tubular cover member 58, and the cover member 58 would be appropriately connected to the vaporizer adaptor 16 and the closure adaptor 18 to fulfill the function the other conduit.) Preferably, the filling conduit 26 and venting conduit 28 cross over one another, between the closure adaptor 18 and vaporizer adaptor end pin 16, in order to reduce the likelihood of kinking or twisting of these conduits (not shown).

A corrugated flexible region 30 is provided on cover tube 58 to provide flexibility so that the cover tube 58 will flex at that region rather than twisting or kinking. This reduces the likelihood of kinking of filling and venting tubes 26 and 28 and provides flexibility for the connecting tube assembly 12 as a whole. The material of the filling and venting tubes is preferably polytetrafluoroethylene because of its inertness and its resistance to permeation by anesthetic vapors. The cover tube 58 is preferably polyvinylchloride for flexibility and ease of forming the corrugated flexible region 30.

The vaporizer adaptor or end pin 16 is attached to one end of the cover member 58 and is of a standard configuration to mate with a vaporizer. The pin 16 is shown in FIGS. 1 and 2 as being a rectilinear block. The vaporizer adaptor end pin 16 has a circular cylindrical portion 38 extending from one end for fitting into the cover tube 58. The pin 16 may be provided in other shapes to fit the particular shape of the receiving connector or transfer device on the vaporizer. Often, vaporizers are designed with receiving connectors of a specific shape to minimize the possibility of error when attaching anesthetic containers. The connector tube 12 can therefore be provided with a specific vaporizer adaptor end pin 16 which is specific to the vaporizer with which it is to be used.

The pin 16 can also be provided with a recessed groove 39 (FIG. 1A) along one corner edge thereby providing an asymmetric shape to ensure correct orientation within the corresponding connector portion of the particular vaporizer with which it is to be used. This is preferably designed according to the applicable standard of the International Standardization Organization "I.S.O.").

The vaporizer adapter end pin 16 is matingly attached to the cover tube 58 by means of a metal piece 36 externally crimped over, and constricting, the cover tube 58 around the cylindrical portion 38 of the vaporizer adaptor end pin 16. The vaporizer adaptor 16 is also provided with filling channel 32 and venting channel 34 in direct communication with the filling member or conduit 26 and the venting member or conduit 28, respectively.

The filling member 26 is press fitted within the filling channel 32, and venting member 28 is press fitted within the venting channel 34. An exit hole 42 of the filling channel 32 and an exit hole 40 of the venting channel 34 are positioned in a standard orientation for the vaporizers with which the device is to be used so as to communicate, respectively, with the portion the vaporizer to be filled and with the portion of the vaporizer from which air is to be evacuated.

A blocking cap 46 with plugs or stubs 48 and 50 is provided for blocking the exit holes 40 and 42 prior to, and following, use of the system. The stubs 48 and 50 may be inserted within the exit holes 40 and 42, respectively, to block them. A retaining leash 52 extends between the tube 12 and the blocking cap 46 and prevents separation of the blocking cap 46 from the tube 12 when the blocking cap 46 is removed from vaporizer adaptor end pin 16.

The closure adaptor 18 is generally an ovate cylinder in shape with a circular cylindrical portion 54 (FIG. 2) extending from one end. The cylindrical portion 54 is sized to fit within the tube 58 and to mate with it by means of a metal piece 56 which is crimped externally over the cover tube 58 to constrict the cover tube 58 around the cylindrical portion 54 of the closure adaptor 18. The closure adaptor 18 is also provided with a filling channel 61 in direct communication with the filling member or conduit 26 and is provided with a venting channel 63 in direct communication with the venting member or conduit 28 through the closure adaptor 18. The filling member 26 and venting member 28 are press fitted within the filling channel 60 and the venting channel 62, respectively.

The filling and venting channels 61 and 63 terminate at piercing members 72 and 74, respectively. The piercing members 72 and 74 are hollow, needle like members preferably formed as part of the closure adaptor 18 (although they could be separate inserts of metal or a hard plastic if desired).

The generally ovate shape 71 of the end of closure adaptor 18 is chosen to mate with a corresponding shape of the closure 20, it being understood that containers of anesthetic may have closures of particular shapes to avoid accidents whereby the container is hooked up to an incorrect vaporizer.

Two seals 60 and 62 are marginally recessed from the upper surface of the closure 20. The two seals 60 and 62 are generally round, frangible disks and are integrally formed with the closure 20. A one-way check valve 80 can be press fit within venting channel 76 if desired to ensure that no liquid can flow through it into the vent tube 28.

Also located on the closure 20 and closure adaptor 18 are locking means 68 and 70, respectively. The closure locking means 68 are located on the exterior surface of the closure 20 and generally are of the form of an outwardly projecting wedge. Closure adaptor locking means 70 are located on corresponding positions on the closure adaptor 18 and are generally of the form of a recessed edge. Engagement of the closure 20 with the closure adaptor 18 causes the wedge shape to engage the recessed edge, thereby preventing separation of the connector tube 12 from the closure 20.

Dust caps 64 and 66 are provided to cover the open ends of the closure 20 and closure adaptor 18, respectively, to maintain internal surface cleanliness until it is desired to mate the closure adaptor 18 to the closure 20.

In the operating room, the anesthetist chooses the appropriate anesthetic for administration from various supply containers each fitted with a closure 20, check valve 80, and dust cap 64. A connector 12 which has a closure adaptor 18 designed to mate with the particular closure 20 of the chosen anesthetic is removed from its packaging. The dust caps 64 and 66 are removed, and the closure adaptor 18 is inserted over the closure 20 such that the locking means 68 and 70 are engaged. The engagement action causes the piercing means 72 and 74 to engage the seals 60 and 62, respectively, thereby causing perforation of the seals. The blocking cap 46 is then removed, and the vaporizer adaptor end pin 16 is inserted within the vaporizer. The pin 16 can be removably held in place on the vaporizer with a strap (not shown) passed around the pin 16 and secured so that the pin 16 cannot be disengaged from the vaporizer. Anesthetic can then flow between said container 14 and the vaporizer.

During use in a medical operation, the anesthetist may also elect to administer other anesthetics. In changing anesthetics, the vaporizer adaptor 16 is removed from the vaporizer, and the blocking cap 46 is reinserted into holes 40 and 42. Another anesthetic may then be administered using a second system of a connector 12 and an anesthetic bottle 14, the connector having a vaporizer adaptor end pin 16 sized to mate with the same vaporizer.

To disassemble the system following use, the vaporizer adaptor 16 is removed from the vaporizer and the blocking cap 46 is reinserted into holes 40 and 42. The entire system, including the anesthetic container, is then thrown away without further disassembly.

Figure 4:
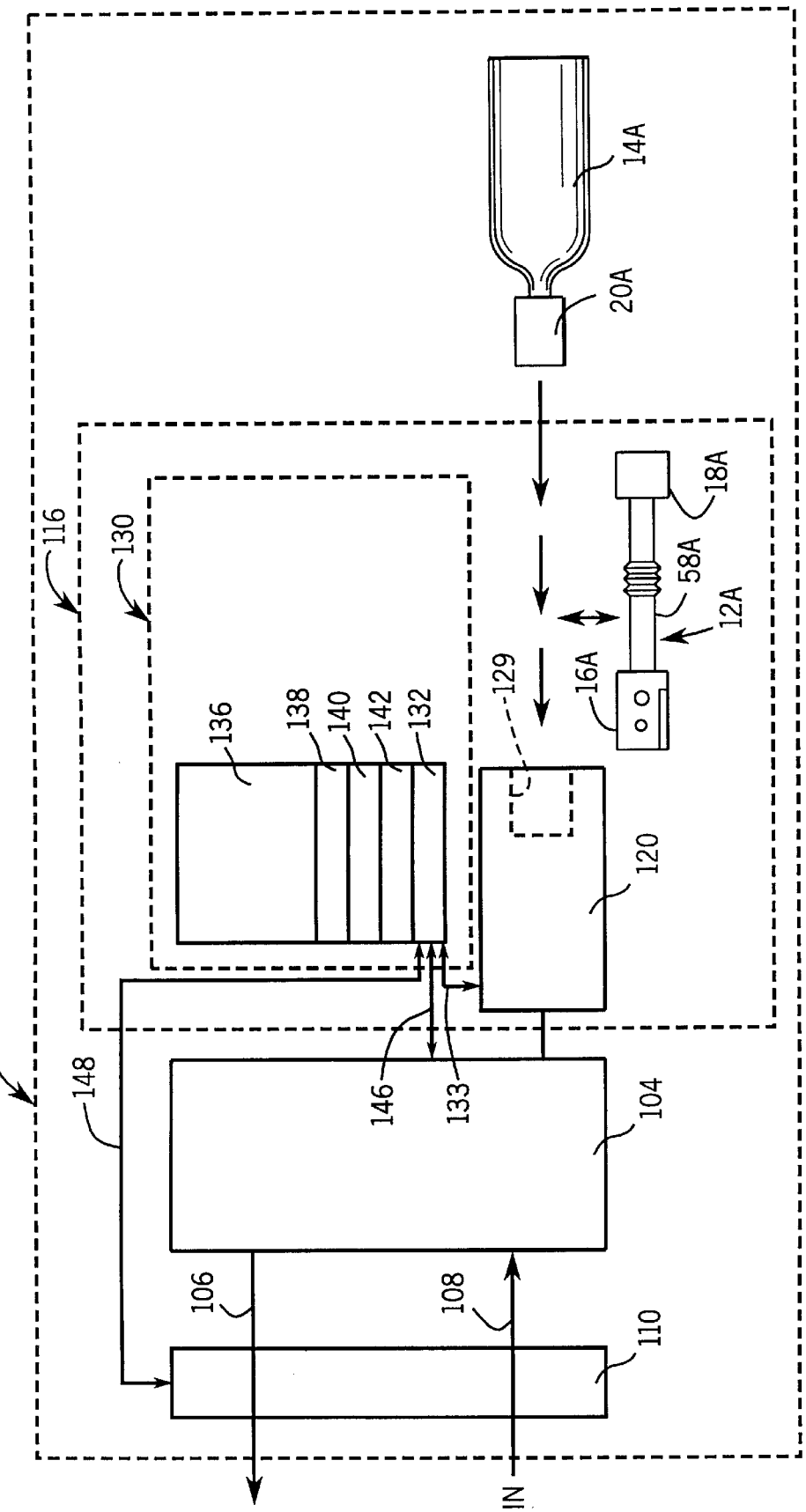
FIG. 4 is a schematic diagram illustrating some general features of certain aspects of one end of the present invention.

An improved system that can incorporate features of the above-discussed prior art connector tube and/or anesthetic container closure is illustrated in FIG. 4. Components of a system for filling a vaporizer with anesthetic are schematically illustrated in FIG. 4 as part of a filling system 102 which is adapted to receive an anesthetic container or bottle 14A having a cap or closure 20A. The bottle 14A and closure 20A, in a preferred form, are similar or identical to the bottle 14 and closure 20, respectively, described above with reference to FIGS. 1 and 3. However, it is contemplated that the closure 20A may include certain modifications discussed hereinafter in detail.

The system 102 includes a vaporizer 104 which, in operation, vaporizes the liquid anesthetic and mixes it with other gases, such as oxygen and nitrous oxide, to provide a gas mixture as indicated by the process flow arrow 106. An appropriate supply of such other gas or mixture of gases is supplied to the vaporizer as indicated in the process flow arrow 108.

The gases flowing into and out of the vaporizer 104 are controlled by a gas parameter control system 110. The vaporizer 104 and gas parameter control system 110 may have a special or conventional design to control the anesthetic in the conventional manner as is understood by those of ordinary skill in the art. Except for certain operational controls or interlocks and monitoring systems that may be provided for use with some forms of the present invention, the detailed design and operation of the vaporizer 104 and gas parameter control system 110 form no part of the present invention.

FIG. 4 schematically illustrates a transfer system 116 for transferring the anesthetic liquid from the container 14A to the vaporizer 104. The system may preferably also allow the return of anesthetic liquid from the vaporizer reservoir to the container 14A.

The transfer system 116 includes a transfer device 120 which may be incorporated as an integral part of the vaporizer 104 or which may be a substantially separate device that can be temporarily or permanently mounted or attached to the vaporizer 104.

The transfer device, whether fabricated as an integral part of the vaporizer 104 or separately provided and mounted to the vaporizer 104, defines a receiving station that typically includes a recess, socket, or other type of holding assembly 129 for receiving either a container closure (e.g., closure 20A in FIG. 4) or an end of a transfer tube (such as tube 12A) interposed as an intermediate connecting device between the container 14A and the transfer device 120.

The tube 12A may be generally similar to the tube assembly 12 described above in detail with reference to FIGS. 1–3. It will be appreciated, however, that the transfer tube 12A may incorporate additional features described in detail hereinafter. The transfer tube 12A can include an adaptor, coupling, or end pin 16A joined via a tubular member 58A to a closure adaptor 18A. The pin 16A, tubular member 58A, and adaptor 18A may be similar to the pin 16, tubular member 58, and adaptor 18, respectively, described above in detail in reference to FIGS. 1–3. However, in some forms of the present invention, the pin 16A and/or adaptor 18A, as well as the container closure 20A, may be modified as described in detail hereinafter to incorporate additional novel features. Among the novel features that may be included in the transfer tube 12A and in the bottle closure 20A are indicia which provide information upon proper connection of the transfer system components.

Some forms of the invention, as will be explained in more detail hereinafter, include unique, mechanical engaging structures and clamping assemblies as part of the transfer device 120 for accommodating connection of only selected, matching components and for providing a secure, leak-tight assembly.

Another aspect of the invention includes a connection response system 130 which processes information about the connection for use in a variety of ways. In a preferred embodiment, the response system 130 incorporates electronic or electrical systems for processing information relative to the components and/or connections as sensed optically, magnetically, electronically, electrically, etc. Preferably, the response system 130 includes an interface system 132 which is associated with, or includes, a sensor for sensing a feature or indicium associated with a properly connected component. In FIG. 4, the transfer of information from the components in the transfer device to the interface system 132 is represented by the line 133. A means is provided for generating a signal in response to the sensing of the interface condition. The signal may be employed for producing a visual display 136, and/or may be employed in some other monitoring system 138, in a recording system 140, in a control system 142, etc.

The interface characteristic sensed by the interface system 132 when the connections are properly made may thus serve to at least indicate the establishment of a proper connection. Further, various features or indicia sensed by the interface system 132 can also be representative of a characteristic of the container 14A, such as container size, anesthetic type, and expiration date, as well as the proper position of the container. Such characteristics can be visually or aurally displayed in the display 136, monitored in the monitor 138, recorded in the recorder 140, and/or used as inputs in an interlock or control system 142 affecting the operation of the vaporizer 104. For example, unless the proper size and type of the container 14A are sensed by the system 132, the vaporizer 104 could be prevented from operating. Further, the recording system 140 could record the type of container and anesthetic used, the number of times such a container is connected, etc.

Such information can be correlated with the operation of the vaporizer 104 and with internal clock systems so as to provide a history of operation and anesthetic usage in terms of, for example, cumulative operating time, cumulative throughput for one or more specific types of anesthetic, operating conditions, operating times for each container connected to the system, etc. This can provide valuable information as part of a record of the delivery of anesthetics to specific patients as well as apparatus history and component life cycle data, product usage data, etc.

Optional control of the vaporizer 104 can be effected through the interface system 132 as schematically indicated in FIG. 4 by the control signal 146. The gas parameter control system 110 may be similarly controlled as schematically illustrated in FIG. 4 by the control line 148. In addition to controlling the vaporizer 104 and gas parameter control 110, other components of an anesthesia system may be controlled, including the respirator, scavenging systems, the fresh gas mixer, etc. This is possible through the interface system 132 with suitable accessory instrumentation and controls.

The display 136 may also include appropriate alarm signals or alert signals as well as advice and status messages. Further, automatic setting of operational parameters of the vaporizer is thus possible according to the specific anesthetic and/or specific anesthetic container being used.

Various embodiments of the transfer tube 12A are illustrated in FIGS. 5–14 and are next described in detail. One embodiment that incorporates a unique mechanical coding, keying, or structural configuration is illustrated in FIGS. 5–7 as employed with a transfer tube 12B.

The tube 12B, in a preferred form, includes a coupling member or adaptor end pin 16B and a tubular member 58B which joins the pin 16B with a container closure adaptor (not illustrated) identical to the adaptor 18 described above with reference to the embodiment illustrated in FIGS. 1–3. The internal structures of the pin 16B and of the cover member 58B are identical to the structures in the pin 16 and member 58 described above with reference to the embodiment illustrated in FIGS. 1–3. However, in the embodiment illustrated in FIGS. 5–7, a unique, additional mechanical coding or keying system is provided to supplement the conventional keying system.

The conventional keying system in the pin 16B includes a notch 39B. The notch 39B, in the preferred form, is identical to the notch 39 described above with reference to the embodiment illustrated in FIG. 1. The configuration of the notch 39B conforms to the I.S.O. standards and preferably is normalized by the I.S.O. Standard No. 5360. This notch configuration on the pin 16B varies according to the specific anesthetic and is adapted to mate with a receiving I.S.O. normalized filling port on the vaporizer intended to be used with the specific anesthetic. Thus, with reference to FIG. 4, the transfer device 120 would include an appropriate key for mating with the notch 39B, and the transfer device 120 may be an integral part of the vaporizer 104. Alternatively, such a keyed transfer device 120 may be a separate device mounted to, and appropriately connected with, the vaporizer 104.

The coupling or pin 16B includes the additional key system in the form of a pair of oppositely extending flanges 150 and 152. The flange 150 has a generally arcuate or partially cylindrical surface 154, and the flange 152 has a generally arcuate of partially cylindrical surface 156. Further, the flange 150 defines a recessed notch 158 having an arcuate or partially cylindrical rear surface 160. Similarly, the flange 152 defines a recessed notch 162 having an arcuate or partially cylindrical rear surface 164.

The recess 158 is deeper than the recess 162. This thus provides an asymmetrical flange key configuration. A number of different pins 16B can be made with different recess depths, and each particular recess depth arrangement can be associated with a characteristic of the anesthetic container or anesthetic, such as the identity of the anesthetic manufacturer, the type or size of container to which the tube 12B is adapted to be connected, etc.

The filling port on the vaporizer (in the integral or separate transfer device 120 as illustrated in FIG. 4) would, of course, be provided with a mating, receiving key configuration. This would prevent connection of the pin 16B to the vaporizer unless the configuration of both the I.S.O. notch 39B and the additional keyed flanges 150 and 152 are the proper ones for use with the particular vaporizer.

The transfer device 120 (within the vaporizer or attached to the vaporizer) may be provided with appropriate mechanical sensing or engaging structures responsive to the shapes of the keyed flanges 150 and 152 for sensing the presence of the keyed flanges as part of an interface system, such as the interface system 130 discussed above with reference to FIG. 4. As previously explained, such an interface system can respond to the appropriate key configuration to control the operation of the vaporizer or other anesthesia equipment components, to monitor information and operation, to record information, to display status messages, alarms, etc.

Figure 8:
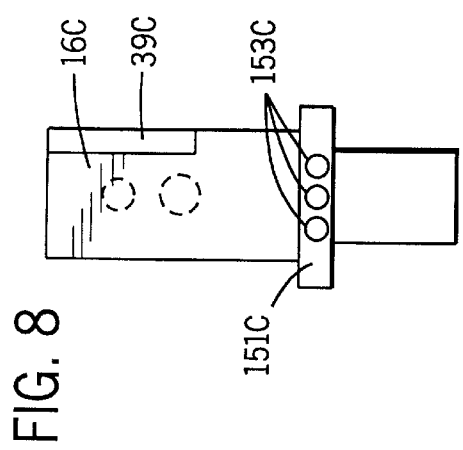

Another embodiment of a tube assembly and pin is illustrated in FIG. 8 and identified therein generally by the reference number 16C. The pin 16C is adapted to be mounted to the end of a connecting tube assembly, such as in place of the pin 16A illustrated in FIG. 4 or in place of the pin 16B illustrated in FIGS. 5-7.

The pin 16C includes a standard, anesthetic-specific I.S.O. notch 39C identical to the notch 39B described above with reference to the embodiment illustrated in FIGS. 5–7. The pin 16C also has a flange 151C which includes indicia in the form of additional structural or mechanical keys 153C, such as recesses or projections.

Suitable mating components are provided in the vaporizer transfer device (such as the transfer device 120 illustrated in FIG. 4 as being on or in the vaporizer 104) to engage and/or sense the flange 151C and/or keys 153C. The flange 151C and/or keys 153C have a coded configuration and can be employed to provide an indication of the establishment of a proper connection or other information such as container size, expiration date, etc. These features may be used by the response system 130 described above with reference to FIG. 4 for monitoring, recording, etc. as explained previously. Switches or other receiving devices can be actuated or sensed by the flange 151C and/or keys 153C to effect transfer of the information to the system 130.

Figure 9:
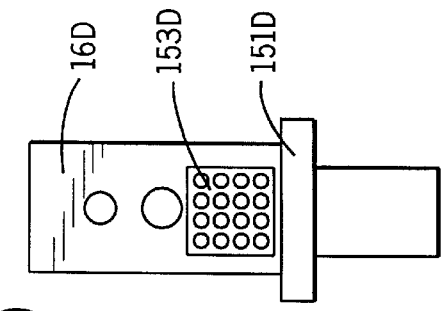

FIG. 9 illustrates another form of a pin which is adapted to be mounted at the end of a tube assembly, such as the tube assembly 12A illustrated in FIG. 4. The pin 16D includes indicia in the form of an electrical or electro-mechanical code or keying system 153D. This can include, for example, sets of electrical contacts which are connected in a specific pattern and which are adapted to be engaged with mating, electrical terminals within the transfer device 120 on or in the vaporizer 104 (FIG. 4). Completed electrical circuits cannot be established unless the pin 16D is properly inserted into the transfer device 120. Thus, establishment of the electrical circuits is an indication that the proper connection has been made.

In addition, the pattern of electrical circuits can be assigned a particular coding relationship which can be associated with particular parameters, such as the type of anesthetic, the size of the container, the expiration date of the anesthetic within the container, etc. These features, as well as other features, may be employed by the response system 130 illustrated in FIG. 4 for use, where desired, in operating interlocks, in monitoring and warning systems, in recording systems, in control systems, and the like as explained above in detail with respect to FIG. 4.

The pin 16D may include a flange 151D for being engaged by a suitable receiving structure within the transfer device 120 (FIG. 4). The flange 151D may, if desired, also engage switches or be sensed by sensing devices within the transfer device as a means of providing additional indicia, coding, or keying.

Figure 10:
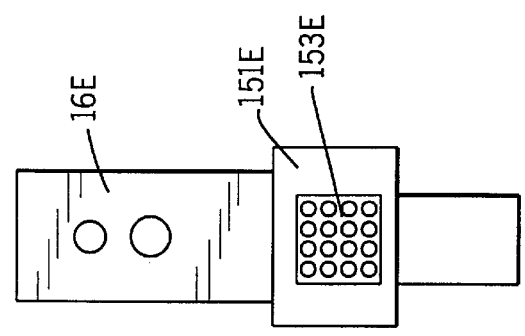

Another embodiment of a pin is designated generally by the reference number 16E in FIG. 10. The pin 16E is very similar to the pin 16D in FIG. 9. However, the pin 16E has a much thicker flange 151E on which is located an electrical or electro-mechanical keying system 153E. The system 153E may be characterized as indicia which contains information that can be sensed by a suitable sensing interface system 132 of a response system 130 (FIG. 4) in the same manner as in the keying system 153D described above with reference to FIG. 9.

Figure 11:
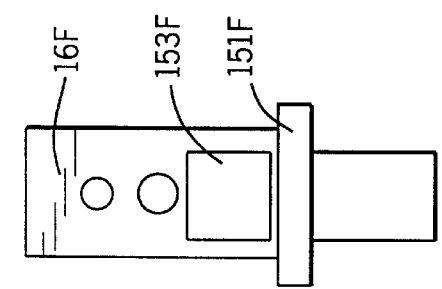
FIGS. 8–12 are simplified, diagrammatic side elevational views of different modified forms of the connector tube end pin illustrated in FIGS. 5–7.
Figure 12:
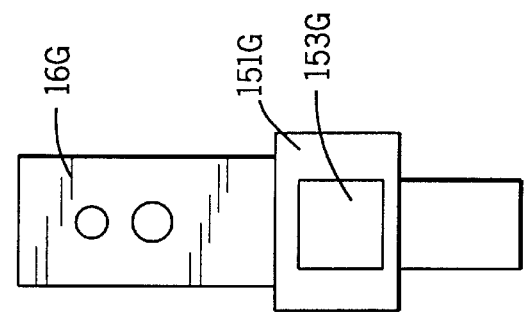

FIGS. 11 and 12 illustrate additional embodiments of a coupling member or pin which incorporate electronic keys or indicia. In particular, FIG. 11 illustrates a pin 16F with a lower flange 151F. Mounted on or in the pin 16F is an electronic key 153F. The electronic key 153F may be a conventional surface acoustic wave device, magnetic data-storage medium, etc. In a presently contemplated preferred embodiment, the key 153F may be a radio-frequency device that can be sensed by a radio-frequency sensor, such as that sold by Tagman Italia S.r.l.

When the pin 16F is inserted into the transfer device (120 in FIG. 4) in the vaporizer (104 in FIG. 4), the key 153F can be sensed (i.e., read) by the sensing device installed within the transfer device. The information can then be used (as described above in detail with reference to FIGS. 4–10) to confirm the establishment of the connection or to provide additional information for use in the response system (130 in FIG. 4). This can include identification of anesthetic type, container size, expiration date, etc.

A modification of the pin 16F is illustrated in FIG. 12 wherein the modified pin is designated generally by the reference number 16G. The pin 16G includes an enlarged flange 151G. Indicia in the form of an electronic key 153G is mounted on or in the flange 151G. The operation of the pin 116G in conjunction with a transfer device is substantially the same as described above with respect to the pin 16F illustrated in FIG. 11. However, the transfer device for receiving the pin 16G would, of course, necessarily be modified to receive the larger (thicker) flange 151G.

The electrical or electronic keys (e.g., 153D, 153E, 153F, and 153G) and the associated sensing systems in the receiving transfer device may incorporate any suitable, special or conventional design. Accordingly, the detailed designs of the electrical or electronic key systems per se illustrated in FIGS. 9–12 form no part of the present invention.

FIGS. 13 and 14 illustrate another form of the present invention which employs a tube assembly similar to the tube assemblies 12 and 12A discussed above with reference to FIGS. 1–4. The modified tube assembly is designated generally by the reference number 12H in FIGS. 13 and 14. One end of the tube assembly 12H is adapted to be received in a port defined in a transfer device 120H which is part of a vaporizer (such as the vaporizer 104 described above in reference to FIG. 4).

The other end of the tube assembly 12H is adapted to be connected to a container 14H which is a modification of the container 14 described above with reference to FIGS. 1–4. A closure 20H is mounted on the container 14H, and the closure has an ovate projection 21H for being connected with the tube assembly 12H. Each side of the projection 21H includes a locking member 68H which is engaged by the end of the tube assembly 12H.

The closure 20H has an internal structure substantially identical to the internal structure of the closure 20 described with reference to FIGS. 1–3. However, an exterior side portion of the projection 21H is modified to include indicia in the form of one or more dots or spots. In the preferred embodiment illustrated in FIG. 14, two colored dots 23H are provided on the surface of the closure projection 21H.

The tube assembly 12H includes a closure adaptor 18H adapted to mate with the container closure projection 21H. The structure of the closure adaptor 18H is similar to the closure adaptor 18 described above with reference to the embodiment illustrated in FIGS. 1–3. However, the closure adaptor 18H includes a fiber optic sensor system for sensing the indicia 23H on the closure 20H. In particular, in the embodiment illustrated in FIG. 14, the ends of two optical fibers 19H are mounted in bores in the wall of the closure adaptor 18H. The optical fibers are arranged to be in registry with the colored dots or spots 23H on the closure 20H when the closure adaptor 18H is properly connected to the projection 21H of the closure 20H. The optical fibers may be connected to a suitable monitoring or control system (e.g., the response system 130 illustrated in FIG. 4). The optical fibers 19H may be permanently attached to such a monitoring or control system or may be designed to be connected and disconnected from either the monitoring and control system or from the closure adaptor 18H.

When the proper connection is established between the closure adaptor 18H and the closure 20H, the optical fibers transmit the light from the colored dots 23H to the monitoring and/or control system. An appropriate signal can be generated when the light from the colored dots is received to provide an indication that a proper connection has been made.

The system illustrated in FIG. 14 provides a key or code system that allows a single type of tube assembly 12H to be used with a variety of anesthetics. Further, the system permits a single type of closure 20H to be used with a variety of anesthetics because only the colors of the dots or spots 23H need be different for each type of anesthetic. The sensing and control system, through conventional processes well known to those of ordinary skill in the art, can distinguish among various colors. For a particular type of vaporizer, only a particular, predetermined color or set of colors are recognized by the sensor system. Recognition of the appropriate color or colors generates a signal permitting operation of the vaporizer and/or displaying appropriate status information (such as the type of anesthetic, size of the container, etc.).

If the predetermined color or colors are not recognized, the vaporizer is prevented from operating and/or appropriate warning or alarm messages are displayed.

In addition to, or instead of, the fiber optic system for sensing colored dots on the container closure, the tube assembly 12H can be provided with a similar system on the end of the tube assembly 12H that is connected with the transfer device 120H on or in the vaporizer as illustrated in FIG. 13. The vaporizer end of the tube assembly tube 12H includes a pin 16H which can be substantially identical to the pin 16B described above with reference to the embodiment illustrated in FIGS. 5–7. Thus, the pin 16H can include one or more mechanical keys, such as an I.S.O. notch 39H.

However, the pin 16H also includes indicia on the top, upwardly facing surface. In the preferred embodiment illustrated, the indicia are in the form of colored dots or spots 27H. The spots 27H are arranged in a predetermined array and have a specific color or colors.

Within the receiving port in the transfer device 120H is a sensing unit terminating in a block 29H. A plurality of optical fibers 31H extend through the block 29H. The ends of the optical fibers 31H are arranged to be in registry with the colored spots 27H when the pin 16H is properly inserted into the receiving port. The optical fibers 31H transmit the light signals from the spots 27H, and this information can be processed as desired (e.g., in the response system 130 illustrated in FIG. 4 discussed above) to provide status information and/or to control operation of the vaporizer or other equipment. The dots or spots 27H can provide coded information with respect to the type of anesthetic, container size, etc. In some applications, it may be desirable to provide the tube assembly 12H as a unit permanently attached to the container closure 20H.

As with the fiber optic system 19H discussed above with respect to FIG. 14, the design of the fiber optic sensor 29H and of associated control systems may employ suitable conventional technology known to those of ordinary skill in the art, the details of which form no part of the present invention. Optical fiber sensing systems which may be employed as presently contemplated include those sold by Omron in Milan, Italy, Sensormatic S.r.l. in Bologna, Italy, and Keyence in Como, Italy.

Figure 16:
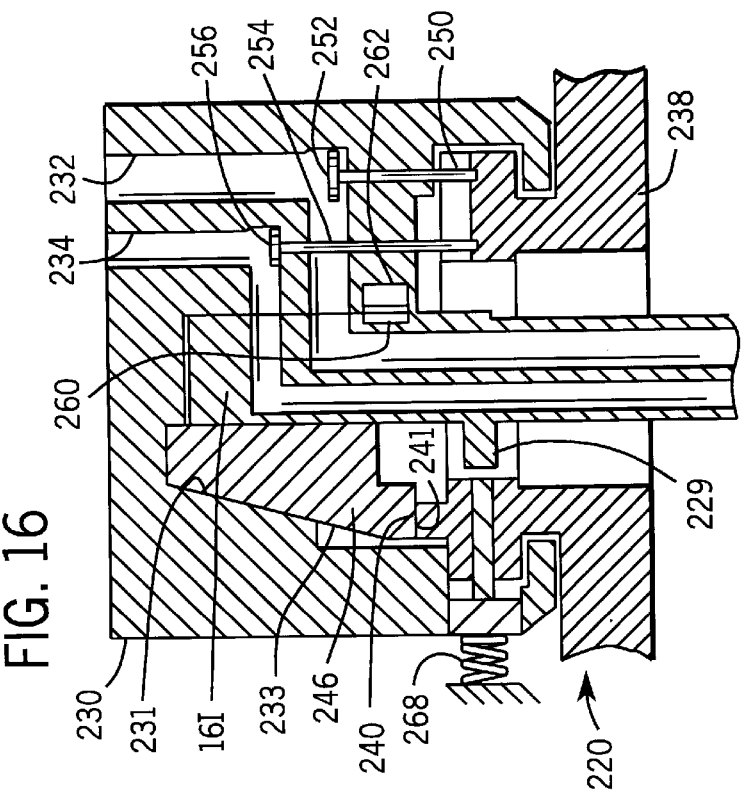
FIGS. 15 and 16 are simplified, partially diagrammatic, cross-sectional views of another form of a connector tube end pin and a transfer device.
Figure 15:
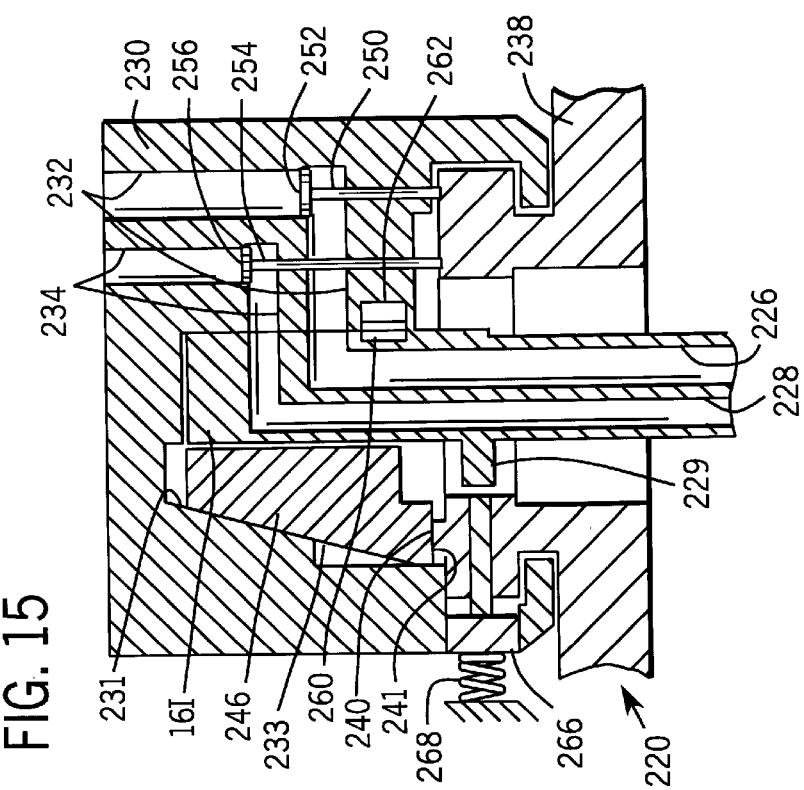

A unique transfer device 220 which may be employed on or in a vaporizer for engaging an end of a transfer tube assembly is illustrated in FIGS. 15 and 16. A tube assembly end pin 16I is shown inserted into a transfer device 220. The pin 16I may be similar to any of the pins 16, 16A, 16B, 16C, 16D, 16E, 16F, and 16G described above. The pin 16I defines a liquid filling passage 226, and a gas venting passage 228. The pin 16I may also be provided with a latching flange or tab 229. Omitted from FIGS. 16 and 15 for ease of illustration is the transfer tube (e.g., similar or identical to the elements 12 and 58 described above in detail with reference to FIGS. 1 and 2).

The transfer device 220 includes a body 230 which may be mounted on or in a vaporizer (not shown). The body 230 may be provided as an integral part of the vaporizer or may be provided as a separate component for attachment to the vaporizer.

The body defines a liquid fill passage 232 and a gas vent passage 234 which communicate with the pin liquid fill passage 226 and gas vent passage 228, respectively, when the pin is properly inserted in the body 230. The body 230 also defines an internal cavity for receiving a wedge 246. The body 230 has an angled cam surface 231 engaged with an angled cam follower surface 233 on the wedge 246.

The transfer device 220 includes a rotatable member 238 which is mounted to the body 230 and which is adapted to be rotated (via a suitable operating lever or handle not shown) relative to the body 230. The rotatable member 238 includes an inclined or helical cam surface 240 which extends in a circular arc on the end of the member 238. The cam surface 240 engages a cam follower surface 241 on the clamping wedge 246 which is retained within the body 230.

The clamping member 246 is adapted to be moved from a disengaged, unlocked position (FIG. 15) to an engaged locked position (FIG. 16). When the member 238 is rotated, the inclined cam surface 240 drives the wedge 246 from the disengaged position to the engaged position. In the engaged position, as illustrated in FIG. 16, the wedge 246 engages the pin 16I and forces it in tight, sealing engagement with the interior surface of the body 230 at the body passages 232 and 234.

A novel valve assembly is also preferably provided in the transfer device 220. The valve assembly includes a first valve stem 250 and first valve member 252 connected to the valve stem 250. The valve stem 250 is mounted to the rotatable member 238, and the valve member 252 is adapted to occlude the fill passage 232 as illustrated in FIG. 15.

A second valve includes a valve stem 254 mounted to the rotatable member 238 and a valve member 256 mounted to the end of the stem 254 for occluding the gas vent passage 234 as illustrated in FIG. 15. Each valve stem 250 and 254 is slidably received within an associated bore in the transfer device body 230. The end of each stem 250 and 254 is slidably mounted in an arcuate cam track which is inclined so as to define a portion of a helical path. Thus, as the rotatable member 238 is rotated, the cam track forces the valve stems 250 and 254, and hence the valve members 252 and 256, toward the front of the transfer device body 230 so as to open the passages 232 and 234 (FIG. 16).

Preferably, a sensing system is provided for sensing the proper insertion of the pin 16I in the transfer device 220 and/or for providing other information as may be desired (e.g., type of anesthetic, size of the container, etc.). To this end, the pin 16I includes indicia 260. A sensing means 262 for sensing or reading the indicia is mounted within the transfer device body 262. The indicia 260 and sensing means 262 may include, for example, the electrical, electronic, optical, or other systems described above with reference to the embodiments illustrated in FIGS. 9–14. This can include systems such as a laser light scannable bar code record, magnetic data-storage medium, etc.

The transfer device 220 may also include a special mechanical key system which includes the latch lever 229. To this end, an engaging member 266 is disposed within the transfer device body 230 and has a stem with an angled distal end 268 for being engaged by the flange 229 as the pin 16I is inserted into the body 230. The member 266 is normally biased inwardly by a spring 268. When the pin 16I is inserted into the transfer device body 230, the flange 229 on the pin engages the member 266 and forces the member 266 radially outwardly against the spring 268. The movement of the member 266 may be employed to actuate a suitable switch in an interlock, key reading, or other sensing interface system.

FIGS. 17 and 18 illustrate another form of a transfer device which can perform the functions of the transfer device 120 schematically illustrated in FIG. 4 and described above. The transfer device in FIGS. 17 and 18 is designated generally by the reference number 320 and may be an integral part of a vaporizer or may be provided as a separate unit that can be mounted to a vaporizer.

The device 320 is adapted to directly receive a container 14J without requiring the use of an intermediate transfer tube assembly, such as the tube assembly 12 illustrated in FIGS. 1–3 or the tube assembly 12A illustrated in FIG. 4. A closure 20J is mounted on the container 14J and has a structure substantially identical to the closure 20 described above with reference to the embodiment illustrated in FIGS. 1–3. This structure has an external configuration that is defined by a collar 22J and an upwardly extending ovate projection 21J.

The transfer device 320 includes a body 330 disposed within, or mounted on, the vaporizer (such as the vaporizer 104 illustrated in FIG. 4). The body defines a receiving recess, region, or port 331 for the ovate projection 21J of the container closure. The body 330 defines an enlarged recess 333 for the collar 20J. The body 330 also defines a transfer or filling passage 332 and a gas venting passage 334. The passages 332 and 334 communicate with the port 331. A piercing conduit 335 is mounted in the end of the passage 332 and projects into the port 331, and a piercing conduit 337 is mounted at the end of the passage 334 and projects into the port 331. These piercing conduits are adapted to pierce the closure seals in the same manner as described above with reference to the piercing means 72 and 74 illustrated in FIG. 3.

A pair of arcuate clamping flanges 339 are mounted about 180 degrees apart in receiving cavities 340 defined in the body 330. Each clamping member 339 is biased radially outwardly by a compression spring 342.

A rotatable member 338 is mounted for rotation in the body 330 radially outwardly of the clamping members 342. The member 338 is rotatable about a central axis coincident with the longitudinal axis of the container 14J. A handle (not shown) may be provided to rotate the member 338.

The rotatable member 338 defines a radially inwardly facing camming surface 344. The camming surface 344 does not have a constant radius, but rather, the distance between the rotational axis of the rotatable member 338 and the camming surface 344 decreases from a maximum distance (FIG. 17) to a minimum distance (FIG. 18) along a portion of the inner periphery of the rotatable member 338.

The operator can initially position the container 14J in the transfer device 320 as illustrated in FIG. 17 and then axially move the container 14J against the piercing conduits 335 and 337 so that the piercing conduits 335 and 337 are at least partially received in the receiving ports of the closure 20J. At this point the bottom of the closure collar 22J is adjacent the inclined surfaces of the clamping members 339. The rotatable member 338 can then be rotated, and this causes the cam surfaces 344 to engage the clamping members 339 and force the clamping members, against the biasing force of the springs 342, toward the lower edge of the closure collar 22J. As the angled clamping members 339 engage the lower edge of the collar 22J, the collar 22J, and the container 14J connected thereto, are urged further inwardly on the piercing conduits 335 and 337 which pierce the seals within the closure 21J. The clamping members 339 are retained in the radially inwardmost position (FIG. 18) to retain the container 14J in a tight, sealing engagement within the transfer device 320 so that the anesthetic can be transferred to the vaporizer.

A valve system, comprising a first valve stem 350, first valve member 352, second valve stem 354, and second valve member 356, can be provided in the device 320 in substantially the same manner as described above with respect to the valve stem 250, valve member 252, valve stem 254, and valve member 256, respectively, described above with reference to FIGS. 15 and 16.

If desired, the container 14J can be provided with at least one indicium that can be sensed by a sensor in the transfer device 320. In the preferred form contemplated, the indicium is provided as an electronic key 360 on or in the closure 20J. A sensor system, in the form of an electronic reading system 362 is mounted in the transfer device body 330 at the receiving port 331. The indicium 360 and sensing system 362 may include any suitable special or conventional technology, including those discussed above with respect to the indicium 260 and sensor system 262 illustrated in FIGS. 15 and 16.

Additionally, the transfer device 320 may include a special, integral, blocking device. The blocking device includes a suitable, special or conventional sensor system 372 mounted in the transfer device body 330. Such a sensing system 372 may be employed to sense the location of the distal end of the container closure 20J and permit operation of the rotatable member 338 only if the container 14J has been inserted sufficiently far into the transfer device so that the bottom edge of the closure collar 22J will be properly engaged by the clamping members 339 when the rotatable member 338 is rotated. This would prevent opening of the valve members 352 and 356 if the container 14J was not properly disposed within the transfer device 320. Such a system may employ a conventional sensing means such as photoelectric cell sensors, proximity sensors, electronic sensors, and the like. The detailed design and operation of such systems are well known to those of ordinary skill in the art, and the detailed design of such systems forms no part of the present invention.

Figure 19:
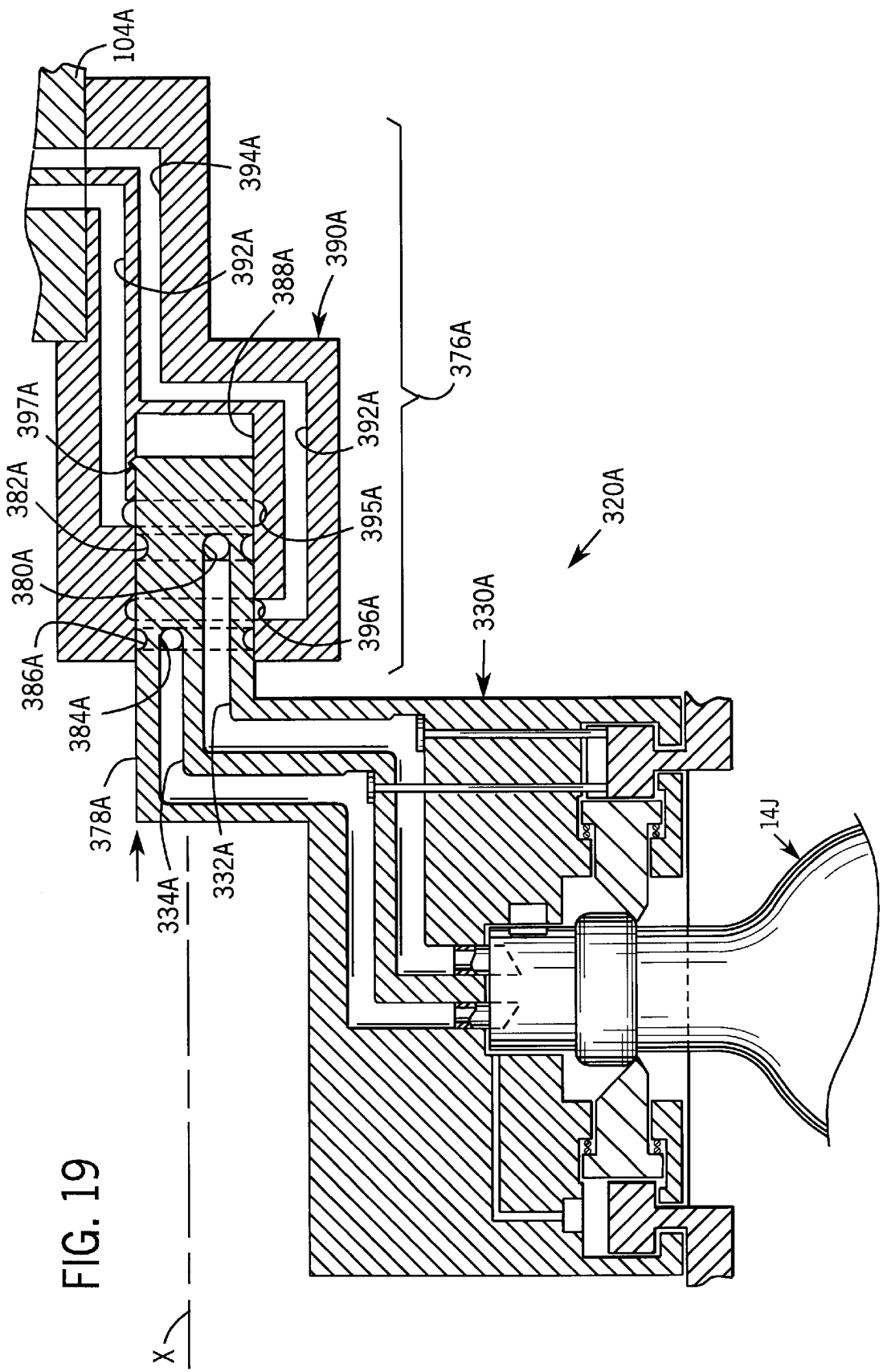
FIG. 19 is a view similar to FIGS. 17 and 18 and shows a modification of the intermediate transfer device in FIGS. 17 and 18.

FIG. 19 illustrates a modification of the transfer device 320 illustrated in FIGS. 17 and 18. The transfer device illustrated in FIG. 19 is designated generally by the reference number 320A. The transfer device 320A is adapted to receive the container 14J described above in detail with reference to FIGS. 17 and 18. The transfer device 320A includes a special secondary valve system 376 at the discharge end of the device. The remaining portion of the device 320A has the same internal structure as, and operates in the same manner as, the transfer device 320 described above with reference to FIGS. 17 and 18.

The secondary valve system 376A is mounted to a projecting portion 378A which has a cylindrical exterior shape. A discharge or transfer passage 332A extends into the cylindrical portion 378A, and a gas vent passage 334A also extends into the cylindrical portion 378A. The transfer passage 332A has a terminal portion 380A which extends transversely through the cylindrical portion 378A and which communicates with an annular groove 382A defined in the exterior cylindrical surface of the cylindrical portion 378A. Similarly, the vent gas passage 334A has a terminal portion 384A extending transversely through the cylindrical portion 378A to an annular groove 386A defined in the exterior cylindrical surface of the cylindrical portion 378A.

The cylindrical portion 378A is mounted within a cylindrical cavity or bore 388A defined in a block 390A. The block 390A is adapted to be mounted to a vaporizer, such as the vaporizer 104 described above with reference to FIG. 4. The block 390A defines a fill passage 392A communicating with a fill passage in the vaporizer 104A, and the block 390A defines a gas vent passage 394A communicating with the gas vent passage defined in the vaporizer 104A. The block fill passage 392A opens to an annular groove 395A defined on the inside surface of the bore 388A, and the block gas vent passage 394A opens to an annular groove 396A defined on the inside surface of the bore 388A.

While the block 390A remains stationary on the vaporizer 104A, the cylindrical portion 378A and attached body 330A can be rotated about 180° on an axis X. FIG. 19 illustrates the device at a first position at one extreme of the rotation range wherein the container 14J is upright and can be connected or disconnected in this orientation.

At the other extreme position of rotation of the body 330A (not illustrated), the container 14J is inverted so that the anesthetic liquid can flow from the container 14J. Preferably, a threaded engagement exists between the cylindrical portion 378A and the stationary block 390A. This is schematically illustrated in FIG. 19 by the thread form 397A on the cylindrical portion 378A within the block bore 388A. The block bore 388A includes a mating thread.

As the body 330A is rotated about the X axis, the threaded engagement causes the cylindrical portion 378A to move along the axis X (to the left or right as viewed in FIG. 19) depending upon whether the threaded engagement is left-hand or right-hand and depending upon the direction of rotation of the body 330A. Rotation of the body 330A in the appropriate direction will cause the cylindrical portion 378A to move along the X axis toward the right as viewed in FIG. 19 so as to align the annular groove 382A with the block annular groove 395A and so as to align the annular groove 386A with the block annular groove 396A. The alignment of the grooves occurs when the body 330A has been rotated about 180° so as to completely invert the container 14J. When the grooves are aligned, the anesthetic flow passages and the gas vent passages are in communication to permit the anesthetic liquid to drain from the container 14J into the vaporizer 104A.

The secondary valve system 376A can be modified, if desired. For example, the annular grooves 395A and 396A could be eliminated, and the passages 392A and 394A could extend directly to the bore 388A. Alternatively, the annular grooves 382A and 386A could be eliminated, and the passages 332A and 334A could extend directly to the bore 388A.

Figure 20:
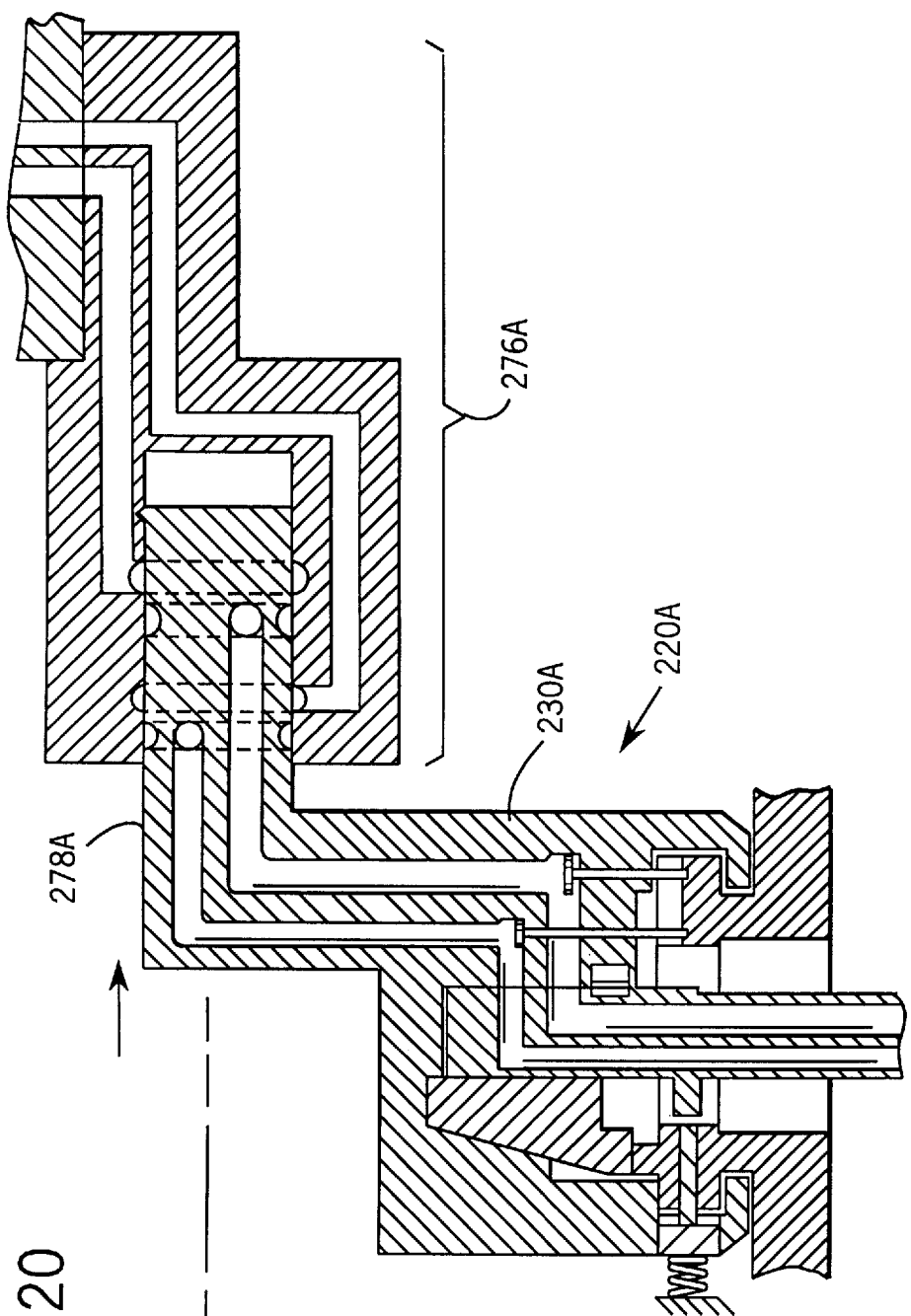
FIG. 20 is a view similar to FIGS. 15 and 16 and shows another modification of the transfer device in FIGS. 15 and 16.

The novel secondary valve system 376A described above with reference to FIG. 19 can be incorporated in the type of transfer device designated 220 in FIGS. 15 and 16. To this end, FIG. 20 illustrates the secondary valve system, designated with a new reference number 276A, in conjunction with a transfer device 220A having a body 230A substantially similar to that described above with reference to the transfer device 220 illustrated in FIGS. 15 and 16.

The body 230A includes an extending cylindrical portion 278A which is received in the secondary valve system 276A in the same manner as described above with reference to the cylindrical portion 378A illustrated in FIG. 19. The operation of the secondary valve system 276A shown in FIG. 20 is identical to the operation of the secondary valve system 376A shown in FIG. 19. The structure of the transfer device body 230A and internal components are the same as the structure and internal components of the body 230 described above with reference to FIGS. 15 and 16. Of course, in FIG. 20, the container (not illustrated) is connected to the transfer device 220A via an intermediate connector tube. Thus, when the transfer device body 230A is rotated between the two extreme positions (the connect/disconnect position illustrated in FIG. 20 and the fill position (not illustrated)), the extending portion of the connecting transfer tube as well as the container must be appropriately supported (by hand or by a suitable structural holder (not illustrated)).

Another embodiment of a transfer device is illustrated in FIGS. 21–42, and this embodiment incorporates a number of novel features which facilitate ease of use and which reduce the likelihood of misuse and improper operation. The device is designated generally by the reference number 420, and in FIGS. 21–28 is shown mounted to a portion of a vaporizer 104B which may be a conventional vaporizer designed to operate as generally described above with reference to the vaporizer 104 illustrated in FIG. 4.

The transfer device 420 is designed to be directly connected to an anesthetic container, such as the type of container 14 discussed above with reference to FIGS. 1–3. The container may be provided with a closure, such as the closure 20 illustrated in FIG. 1, but the closure 20 need not include the locking tabs 68. Otherwise, the internal structure of the closure and of the container may be substantially identical to that described with reference to FIGS. 1–3. Such a container for use with the transfer device 420 is illustrated in FIGS. 24–28 and 30–33 wherein the container is designated generally by the reference number 14L.

Figure 21:
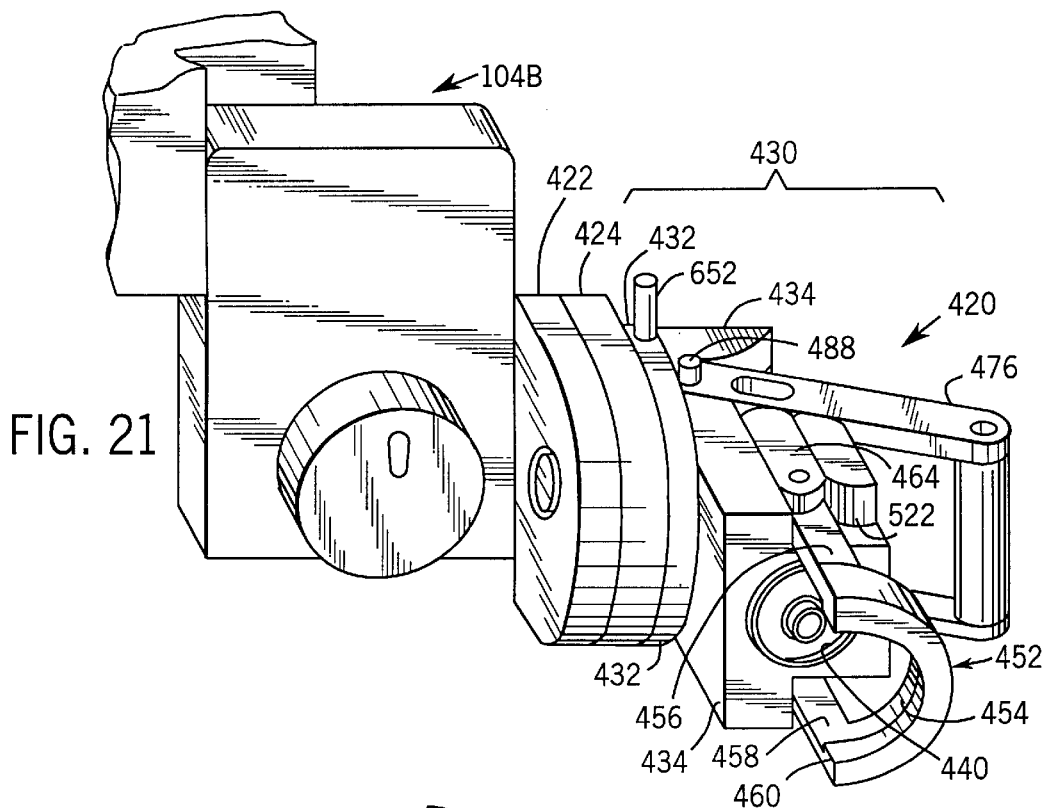
FIG. 21 is a fragmentary, perspective view of one preferred embodiment of the transfer device mounted on a vaporizer.

As shown in FIG. 21, the transfer device includes a rear plate 422, a front plate 424, and a rotatable body 430. The rear plate 422 and front plate 424 are secured together (by means described in detail hereinafter). The plates 422 and 424 are mounted together as a stationary unit in a fixed orientation on the vaporizer 104B at a location on the vaporizer 104B wherein the fluid conduit and gas vent conduit within the vaporizer open to the side of the vaporizer.

The body 430 is mounted on the front surface of the front plate 424 and is rotatable relative to the front plate 424, rear plate 422, and vaporizer 104B. The transfer device body 430 is designed to be rotated about an axis of rotation R (FIG. 22) among a number of orientations. A first "load/unload" or "home" position is illustrated in FIGS. 21–25 wherein the container 14L can be connected to the device 420 and disconnected from the device 420. In this initial position, the body 430 is oriented at an angle relative to the horizontal so that an initially filled container 14L, when properly connected to the device 420, would not be sufficiently tilted so as to permit the container contents C (FIG. 25) to contact the closure seals (e.g., seals such as the seals 60 and 62 in FIG. 3). In this position, the internal fluid transfer passages within the transfer device are occluded by means described in detail hereinafter.

The container 14L is initially connected and clamped to the body 430 in the tilted position illustrated in FIG. 25 by a unique clamping system described in detail hereinafter. After the container 14L has been properly connected and clamped to the transfer device 420, the body 430 can be rotated to a nearly vertical position as illustrated in FIG. 26 wherein the container 14L is substantially inverted. In this nearly vertical position internal passages within the transfer device 420 are closed so as to prevent flow of the liquid anesthetic into the vaporizer 104B. Owing to friction between the components of the transfer device 420, the nearly vertical orientation of the body 430 as illustrated in FIG. 26 is self-maintained.

In order to open the internal passages to the vaporizer 104B, the body 430 must be further rotated (in the clockwise direction as viewed in FIG. 26). In order to further rotate the body 430, a biasing force (provided by a device described in detail hereinafter) must be overcome. The operator must manually rotate the body 430 to overcome the biasing force and must then continue to hold the body 430 in a substantially vertical orientation as illustrated in FIG. 27 wherein the internal passages are open to permit the liquid anesthetic to flow under the influence of gravity into the vaporizer 104B.

After the desired amount of liquid anesthetic has been dispensed into the vaporizer, the body 430 can be released so that it returns to the nearly vertical position illustrated in FIG. 26. Alternatively, the body can be rotated down to the initial load/unload orientation illustrated in FIG. 25. Whenever the operator discontinues holding the body 430 in the vertical position illustrated in FIG. 27, the body is biased back to the nearly vertical position illustrated in FIG. 26 wherein the internal passageways are occluded.

When it is desired to drain liquid anesthetic from the vaporizer reservoir and/or drain the internal passageways in the transfer device 420, the body 430 is rotated to the nearly vertical orientation illustrated in FIG. 28 wherein the container 14L is upright. In the position illustrated in FIG. 28, the internal passages of the transfer device are again open to permit communication between the vaporizer 104B and the container 14L. The anesthetic liquid can then drain into the container 14L under the influence of gravity.

Subsequently, the body 430 can be returned to the initial load/unload position (FIG. 25), and the container 14L can be removed from the transfer device 420.

In the preferred form of the invention, the initial load/unload position of the body 430 is self-maintained (by components described hereinafter in detail), and this position is self-maintained even when a full container of anesthetic is connected to the body 430.

Figure 29:
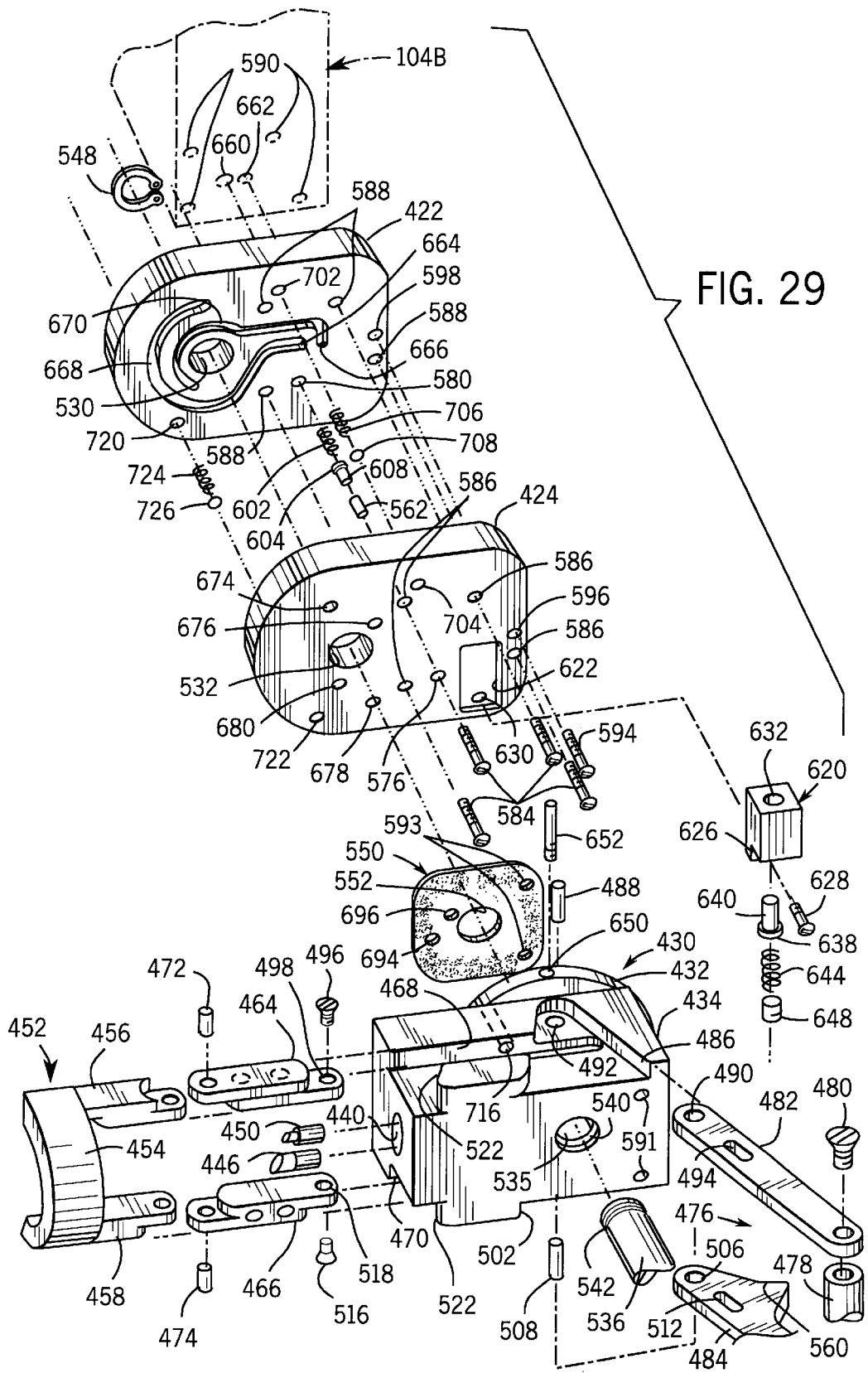
FIG. 29 is an exploded, perspective view of the transfer device.
Figure 40:
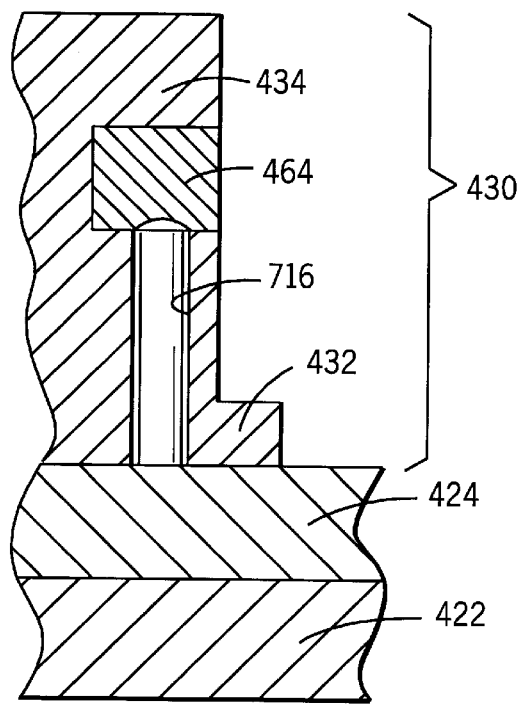
FIG. 40 is an enlarged, fragmentary, cross-sectional taken generally along the plane 40—40 in FIG. 26.

The detailed construction and operation of the transfer device 420 will next be described beginning with the novel mechanism for connecting the container 14L to the transfer device 420. As illustrated in FIG. 29, the body 430 includes a circular bottom plate or portion 432 and a block 434. In the preferred embodiment, the circular portion 432 and block 434 are machined from a single piece of material, such as stainless steel or other suitable material. The block 434 defines a receiving cavity, recess, or port 440 for receiving the container closure.

As illustrated in FIG. 33, the container 14L has a closure 20L with a projecting, ovate portion 21L which is received within the port 440. The internal structure of the closure 20L is substantially identical to the internal structure of the closure 20 described above in detail with reference to FIGS. 1–3.

With continued reference to FIG. 33, a hollow piercing member, spike, or cannula 446 is mounted in the block 434 and has an angled distal end for piercing the closure seal in the liquid filling channel of the closure. Similarly, a hollow piercing member, spike, or cannula 450 is mounted in the body 434 and has a distal end which projects into the port 440 for piercing the container closure seal in the gas venting channel of the closure.

Initially, the container 14L is positioned with the ovate, projecting portion 21L partially inserted into the port 440, but not inserted far enough to effect a piercing of the membrane seals of the closure. After the container has been positioned with the closure 20L partially inserted into the body 434, a clamping system may be engaged with the closure. The clamping system includes a clamp member 452 (FIG. 29) which comprises a semi-cylindrical ring portion 454 and a pair of rearwardly projecting arms 456 and 458. As shown in FIGS. 21 and 33, the inside, distal edge of the semi-cylindrical ring portion 454 defines a shoulder 460 which can engage the lower edge of the container closure 20L when the clamp 452 is moved into an engaging or clamping orientation adjacent a properly positioned container 14L.

Figure 22:
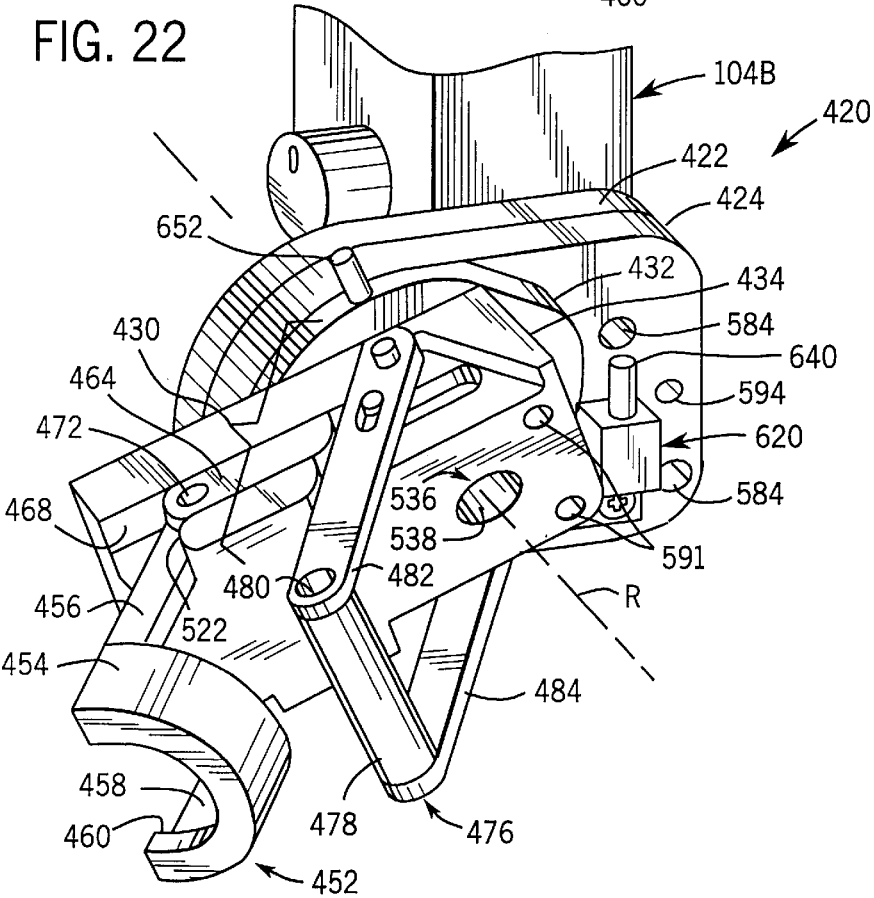
FIG. 22 is another view of the transfer device shown in FIG. 21 taken from a different perspective.

The clamp 452 is movable between an open, release position (FIG. 22) and a closed, clamping position (FIGS. 24, 32, and 33). The clamp 452 is mounted to the block 434 by means of sliding links 464 and 466. As illustrated in FIG. 22 and 29, the link 464 is slidably disposed in a slot 468 defined by the block 434. As illustrated in FIGS. 29 and 30, the other link 466 is slidably disposed in a slot 470 defined in the block 434. The link 464 is pivotally connected to the clamp arm 456 by means of a pin 472 (FIGS. 22 and 29). The link 466 is pivotally connected to the clamp arm 458 by means of a pin 474 (FIGS. 29 and 30).

The clamp links are attached to an operating lever 476 (FIG. 22) which comprises a handlebar 478 secured with screws 480 to a first lever arm 482 and a second lever arm 484. The distal end of the first lever arm 482 is received in a V-shaped recess 486 defined on one side of the block 434 (FIG. 29). The distal end of the first link 482 is mounted with a pin 488 to the block 434. The pin 488 is received in a bore 490 defined by the first link 482 and in a bore 492 defined by the block 434. The first link 482 also defines an elongated slot 494 for receiving the shank of a screw 496 which extends through the slot 494 and is threadingly engaged with the link 464 in a tapped bore 498.

On the other side of the block 434, the second lever 484 is disposed in a recess 502 (FIGS. 29 and 30). The distal end of the lever 484 defines a bore 506. A pin 508 extends through the bore 506 into a receiving bore (not visible) in the block 434. The second lever 484 also defines an elongated slot for receiving the shank of a screw 516 which has a distal end threadingly engaged in a tapped bore 518 (FIG. 29) defined in the link 466.

The operating handle or lever 476 cannot be pivoted from the forward position (FIGS. 22 and 23) to the rearward position (FIGS. 25 and 29) until the clamp 452 is moved from the open, release position (FIGS. 22 and 23) to the closed, engaged position (FIGS. 24 and 30-33). This is the result of, in part, a mechanical interference between the block 434 and the clamp arms 456 and 458. In particular, each side of the block 434 defines a shoulder 522 (FIGS. 21, 22, 29, 30, and 32). When the clamp 452 is in the open, release position (FIG. 22), the clamp arms 456 and 458 rest against the shoulders of 522. In this position, the pivot axis of the clamp 452, as defined by the pins 472 and 474, is near, but rearwardly of, the shoulders 522. If an attempt is made to move the handle 476 rearwardly (from the left to the right as viewed in FIG. 22), sufficient force cannot be generated with the handle lever arms 482 and 484 to slide the links 464 and 466 rearwardly. This is because the block shoulders 522 engage the clamp arms 456 and 458 and because of the relative short moment arms in the linkage. That is, there is only a relatively short distance between the pivot axis of the handle 476 and the connection of the handle 476 to the links 464 and 466, and there is only a relatively short distance between the clamp pivot axis (pins 472 and 474) and the engaging shoulders 522.

In order to move the handle 476 to the rearward position, the clamp 452 must be first manually pivoted from the open, release position (FIGS. 22 and 23) to the closed, engaging position (FIGS. 21 and 25). To this end, after a container 14L has been partially inserted into the transfer device port sufficiently, the clamp 452 can be manually pivoted against the closure so that the clamp shoulder 460 (FIG. 22) engages the end of the container closure 20L. In this position, the clamp arms 456 and 458 are longitudinally aligned with the links 464 and 466. It is now possible to pivot the handle 476 to the rearward position (FIGS. 25 and 30–33).

Although not illustrated, it may be desirable in some cases to provide a suitable interlock mechanism for preventing pivoting of the clamp 452 from the open, release position to the closed, engaging position unless a container 14L is properly positioned for insertion into the transfer device 420.

As the handle 476 is pivoted rearwardly, the clamp 452 is drawn rearwardly to pull the container closure 20L (and attached container 14L) further into the transfer device. As illustrated in FIG. 33, the piercing spikes 446 and 450 then pierce the closure seals and establish communication with the interior of the container 14L.

The body 430 is rotatably mounted to the front plate 424 and rear plate 422 as illustrated in FIGS. 21 and 29. In particular, the rear plate 422 defines a bore 530, the front plate 424 defines a bore 532, and the body 430 defines a bore 534. The bores are aligned in registry to receive a shaft 536. As illustrated in FIG. 37, the shaft 536 includes an enlarged head 538 received in a counter bore 540 in the face of the body 430. The rear end of the shaft 536 defines an annular groove 542 which is disposed within a counter bore 544 in the rear face of the rear plate 422. A conventional C-ring 548 is snap-fitted into the groove 542 to retain the shaft 536 within the assembly.

In order to accommodate rotation of the body 430 relative to the adjacent plate 424 while at the same time providing appropriate fluid seals, a gasket 550 (FIGS. 29 and 37) is disposed between the circular portion 432 of the body 430 and the front plate 424. The gasket 550 defines a bore 552 for receiving the shaft 536.

It will be recalled that the fluid passages in the transfer device are occluded except when the transfer device is in either of the fully vertical positions shown in FIGS. 27 and 28. A novel mechanism is provided for preventing rotation of the body 430 on the shaft 536 away from the home position (FIG. 25) unless and until the handle 476 has been moved fully rearwardly (to the position illustrated in FIGS. 25 and 30–33). This reduces the likelihood that the transfer device 420 would be moved to a position establishing fluid communication with the vaporizer 104B prior to a container 14L being properly engaged with the transfer device.

The novel interlock mechanism that prevents the body 430 from being rotated away from the load/unload position illustrated in FIG. 25 unless the handle 476 is in the rearward position will next be described with reference to FIGS. 29 and 34–36. As shown in FIGS. 29 and 34, the handle second lever 484 defines an outwardly projecting, generally triangularly shaped foot 560. As shown in FIGS. 34–36, the body 430 defines a raised shoulder portion 562 under the foot 560. When the handle 476 is in the forward position (FIG. 34), the foot 560 is at a position furthest away from the shoulder 562. When the handle is moved to the rearward position (e.g., FIG. 30), the foot 560 engages the top of the shoulder 562.

The shoulder 562 defines a bore 564 for receiving a drive pin 566 (FIGS. 35 and 36). An adjacent side of the body 430 rising above the shoulder 566 defines a partially cylindrical cavity 568 for receiving an adjacent portion of the drive pin 566. The body 430 extends laterally outwardly over the cavity 568, as at 570 in FIG. 35, to prevent the drive pin 566 from falling out of the body 434. The bore 564 extends through the body 430 to the front plate 424.

The front plate 424 defines a front bore 574 and an enlarged rear bore or counterbore 576. The smaller diameter bore 574 is visible in the front plate 424 in FIG. 29. The larger counterbore 576 in the front plate 424 opens to the rear plate 422.

The rear plate 422 defines a blind hole 580 in alignment with the enlarged, counterbore 576 of the front plate 424. The rear plate blind hole 580 is visible in FIG. 29.

A compression spring 602 is disposed within the bores 580 and 576 along with a latch pin having a head 604 and a reduced diameter shank 608 which is adapted to extend through the smaller diameter bore 574 in the front plate 424. The distal end of the shank 608 engages the bottom of the drive pin 566 carried in the body 430.

The latching operation of the above described pins 566 and 608 depends on the fixed relationship between the front plate 424 and rear plate 422. The arrangement for fixing these plates together will next be described prior to discussing the latching operation. The rear plate 422 and front plate 424 are fixed together and mounted to the vaporizer 104B to maintain the front plate bore 576 in alignment with the rear plate blind hole 580. To this end, as illustrated in FIG. 29, four screws 584 are installed through holes 593 in the gasket 550, holes 586 in the front plate 424, and holes 588 in the rear plate 422. The screws 584 extend into the vaporizer 104B and are threadingly engaged with four tapped holes 590 in the vaporizer.

The screw receiving holes 586 in the front plate 524 each have an enlarged counterbore for receiving the head of each screw 584 in a recessed arrangement. Two of the screws 584, the two closes to the shaft 536, are covered by the body 430 at all times. Access to these two screws is provided by two bores 591 defined in the body 430 (FIGS. 22 and 29). When the body 430 is rotated to a horizontal position (not illustrated), the holes 591 become registered with the two underlying screw-receiving holes 586 in the front plate 424. This permits the two screws 584 to be installed or removed. The other two screws 586 which are further away from the shaft 536 are not covered by the rotatable body 430 (regardless of the position of the body 430), and these two screws can be readily accessed directly at the front face of the front plate 424.

An additional screw 594 is provided for securing the front plate 424 directly to the rear plate 422. To this end, the front plate 424 defines a bore 596 for accommodating the screw 594, and the rear plate 422 defines a tapped hole 598 for threadingly engaging the screw 594.

Because the front plate 424 and rear plate 422 are fixed together on the vaporizer 104B, the front plate bore 576 remains aligned with the rear plate bore 580. When the operating handle 476 is in the forward position (FIGS. 24, 34 and 35), the latch spring 602 biases the latch pin upwardly so that the pin shank 608 extends part way into the bore 564 in the body. This prevents rotation of the body 430 relative to the front plate 424 and rear plate 422.

However, when the handle 476 is moved to the rearward position (FIGS. 25 and 30), the handle foot 560 engages the drive pin 566 and pushes the drive pin 566 inwardly. As illustrated in FIG. 36, the length of the drive pin 566 is such that the bottom of the drive pin 566 is positioned at the interface between the body 430 and front plate 424 when the handle 476 has been moved to the rearward position with the foot 560 abutting the top of the shoulder 562. This urges the shank 608 of the latch pin downwardly so that the distal end of the shank 608 is also at the mating plane between the body 430 and the face of the front plate 424. The diameter of the drive pin 566 may be somewhat larger than the diameter of the bore 574 in the front plate 424 so as to prevent the possibility of the drive pin 562 entering the front plate bore 574. In this position, the latch pin shank 608 is entirely withdrawn from the body 430, and the body 430 can now be rotated away from the load/unload position illustrated in FIG. 25.

In order to rotate the body 430 to the completely vertical, fill position illustrated in FIG. 27, a novel biasing system must be overcome by the operator who must hold the body 430 with sufficient force to keep it in the fully vertical position as illustrated in FIG. 27. The biasing system is illustrated in more detail in FIGS. 29, 31, and 32. The biasing system includes a block 620 mounted in a recess 622 (FIG. 29) defined in the face of the front plate 424. The block 620 defines a downwardly depending leg 626 having a hole (not visible) through which a mounting screw 628 is disposed. A tapped hole 630 (FIG. 29) is defined in the bottom of the recess 622 in the front plate 424 for threadingly engaging the screw 628 to hold the block 620 on the plate 424.

The top face of the block 620 defines a small bore 632 which communicates with a larger diameter counterbore 634 that extends through the block 620. Disposed within the counterbore 634 is a movable abutment pin having an enlarged head 638 and a reduced diameter shank 640 which extends through the smaller diameter bore 632 and projects above the top face of the block 620. A compression spring 644 is disposed within the counterbore 634 below the movable pin head 638. The spring 644 is retained within the bore 634 by means of a set screw 648 (FIGS. 29 and 34) that is threadingly engaged with a tapped portion of the block 620 at the bottom of the bore 634.

As illustrated in FIG. 29, the circular plate portion 432 of the body 430 defines a tapped bore 650 in the cylindrical side surface for receiving the threaded end of an engaging pin 652. When the body 430 is rotated on the shaft 536 to the position illustrated in FIG. 26, the engaging pin 652 begins to contact the distal end of the movable pin shank 640 projecting from the block 620. Further rotation (in the clockwise direction as viewed in FIG. 26) can only be accomplished by imposing a significantly greater torque on the body 430 so as to overcome the biasing force of the compression spring 644. The operator must maintain this increased torque on the body 430 so long as it is desired to hold the anesthetic container 14L in the vertical position (FIG. 27) for filling the vaporizer. In this position, the fluid passages within the transfer device 420 are open to permit the liquid anesthetic to flow from the inverted container 14L into the vaporizer. If the operator lets go of the container 14L or body 430, then the assembly will be biased to the position shown in FIG. 26 wherein the fluid passages are again occluded.

The novel, internal passage system in the transfer device 420 will next be described with particular reference to FIGS. 29, 31, 33, and 37–39. FIG. 29 shows the vaporizer 104B with a liquid fill passage 660 and a gas vent passage 662. The liquid fill passage 660 is in registry with a fill passage or bore 664 in the rear plate 422, and the vaporizer gas vent passage 662 is in registry with a gas vent passage or bore 666 in the rear plate 422.

The rear plate 422 defines a groove or channel 668 extending from the liquid fill passage 664. The channel 668 has a generally arcuate portion around the shaft receiving bore 530. Similarly, the rear plate 422 defines a groove or channel 670 extending from the gas vent passage 666. The channel 670 has an arcuate portion around the shaft receiving bore 530.

The rear face of the front plate 424 is substantially flat so as to form a seal over the open grooves 668 and 670. The front plate 424 has two pairs of liquid and gas vent passages which extend completely through the front plate 424. One pair includes a liquid passage 674 and a vent passage 676, and the other pair includes a liquid passage 678 and a gas vent passage 680.

The circular plate portion 432 defines a rearwardly facing recess 555 as shown in FIG. 37 for receiving the gasket 550. The recess has a shape that substantially conforms to the shape of the gasket 550 so that the gasket 550 is carried with, and rotates with, the circular plate portion 432 as the body 430 is rotated on the shaft 536.

When the rotatable body 430 is in the vertical orientation with the container 14L inverted as illustrated in FIGS. 27 and 38, the front plate liquid bore 674 and the front plate gas vent bore 676 are open to the interior of the rotatable body 430. To this end, the rotatable body 430 defines a liquid passage 690 and a gas vent passage 692 at the rear face of the body 430 (FIG. 38) to align with the front plate passages 674 and 676, respectively. The gasket 550 defines a liquid passage bore 694 (FIG. 29) in registry with the liquid passage 690 and defines a gas vent bore 696 (FIG. 29) in registry with the gas vent passage 692 (FIG. 29). The body passages 690 and 692 extend at generally right angles to the container port 440 as shown in FIG. 31. The liquid passage 690 communicates with the hollow spike 446, and the gas vent passage 692 communicates with the hollow spike 450.

If the rotatable body 430 is moved away from the position illustrated in FIG. 27, the body liquid passage 690 and gas vent passage 692 move out of registration with the liquid passage 674 and gas vent passage 676, respectively, in the front plate 424. The front plate passages 674 and 676 are then occluded by the gasket 550 which rotates with the body 430.

Thus, if the operator lets go of the body 430 when it is in the position illustrated in FIG. 27, the body 430 will be forced by the previously described biasing spring 640 (FIG. 26) to the non-vertical position shown in FIG. 26 wherein the passages 674 and 676 in the front plate 424 will be occluded as shown in FIG. 37. This is a safety feature which prevents the filling of the vaporizer unless the operator is present to manually maintain the body 430 in the vertical position illustrated in FIG. 27 and can observe the filling of the vaporizer. This reduces the likelihood that the vaporizer could be filled too full or otherwise improperly filled. Further, because the operator must continuously hold the body 430 in the proper position during the filling of the vaporizer with the liquid anesthetic from the inverted anesthetic container 14L, leakage or other malfunctioning of the components will be more readily noticed by the operator.

The front plate pair of passages 674 and 676, as well as the other pair of passages 678 and 680, remain occluded when the rotatable body 430 is moved away from the vertical position illustrated in FIG. 27 until the body 430 is moved to the vertical drain position illustrated in FIG. 28. In this position, the front plate passages 674 and 676 still remain occluded, but the lower pair of passages in the plate 424, liquid passage 678 and gas vent passage 680, are now open to the passages 690 and 692 within the body 430 as illustrated in FIG. 39. In this position, fluid within the transfer device passages, including within the grooves 668 and 670 of the rear plate 422, can completely drain under the influence of gravity through the transfer device and back into the container 14L so as to prevent escape of residual anesthetic to the ambient atmosphere. Indeed, if desired, liquid anesthetic in the vaporizer reservoir can be drained out of the reservoir back through the transfer device into the container 14L.

Subsequently, the body 430 can be rotated back to the load/unload position illustrated in FIG. 25. It will be appreciated that when the operating handle 476 is in the rearward position illustrated in FIGS. 25-28, the container clamp 452 cannot be opened by pulling directly on the clamp 452 or by accidently bumping the clamp 452. This is because the clamp arms 456 and 458 are retracted rearwardly within the grooves 468 and 470, respectively, as shown in FIGS. 30 and 32. This prevents the clamp arms 456 and 458 from pivoting outwardly away from the container closure 20L.

However, the clamp 452 can be disengaged from the container closure 20L if the operating handle 476 is returned to the forward position (FIGS. 21 and 24). In this position, the clamp arms 456 and 458 project sufficiently beyond the body slots 468 and 470 (FIGS. 29, 30 and 31) to accommodate the pivoting of the clamp 452 to the outwardly angled, release position (FIGS. 22 and 23). Subsequently, the container 14L can be pulled out of the transfer device 420 and capped prior to further processing or disposal.

When the operating handle 476 is returned to the forward position as illustrated in FIG. 24, the operating handle lever foot 560 returns to the disengaged position (FIG. 34). The latching pin shank 608 then returns under the influence of the compression spring 602 to the engaging position locking the rotatable body 430 to the front plate 424. This prevents further movement of the rotatable body 430 unless and until the operating handle 476 is again moved to the rearward position (FIG. 25).

In the preferred embodiment illustrated in FIGS. 21–42, it is desirable to provide a tactile sensation as an indication that the rotatable body 430 is in the vertical fill position (FIG. 27) or in the vertical drain position (FIG. 28). To this end, a novel detent system is provided as will next be explained.

Figure 41:
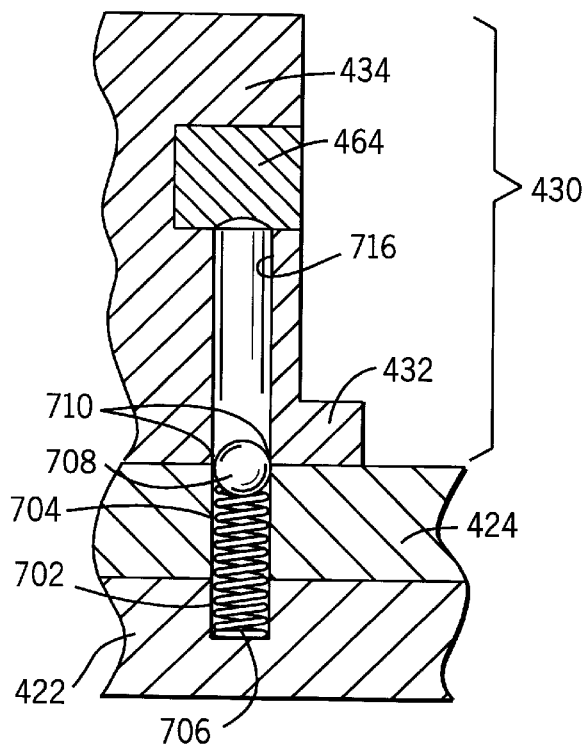
FIG. 41 is an enlarged, fragmentary, cross-sectional view taken generally along the plane 41—41 in FIG. 27.

As illustrated in FIGS. 27, 29, and 41, the rear plate 422 defines a blind bore 702, and the front plate 424 defines a bore 704 in registry with the rear plate bore 702. A compression spring 706 is disposed within the bores 702 and 704. A detente ball 708 is disposed within the bore 704 and is retained within the bore 704 by a lip or peened over portion 710 of the front plate 424 around the bore 704.

As shown in FIG. 41, the rotatable body 430 defines a bore 716 which is adapted to receive a projecting portion of the ball 708 when the body 430 is in the vertical position illustrated in FIG. 27. Until the body 430 is rotated to align the bore 716 with the ball 708, the ball 708 is forced inwardly in the front plate bore 704 against the biasing force of the spring 706.

When the ball 708 is biased outwardly into position in the aligned bore 716 of the rotatable body 430, a small amount of resistance is felt by the operator as an indication that the proper position has been reached. It will be appreciated, however, that the ball 708 does not provide a great amount of resistance to the rotation of the body 430 away from the fully vertical position illustrated in FIGS. 47 and 21. The resistance to such rotation must be relatively low so as to permit the spring-biased drive pin 640 (FIG. 26) to move the body 430 to the non-vertical position whenever the operator releases the body 430 so as to provide an automatic blocking of the internal flow passages as has been explained in detail above.

In the non-vertical position illustrated in FIG. 26, as well as in any other position between the vertical position illustrated in FIG. 27 and the vertical position illustrated in FIG. 28, the rotatable body bore 716 is disengaged from the ball 708. The rotatable body 430 is then rotatable under a substantially constant resistance torque owing to the friction between the assembled components.

Figure 42:
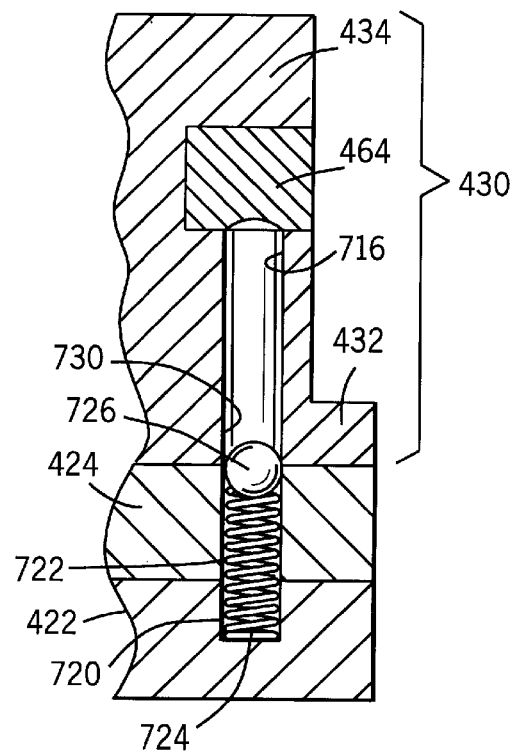
FIG. 42 is an enlarged, fragmentary, cross-sectional view taken generally along the plane 42—42 in FIG. 28.

When the body 430 is rotated to the other vertical position illustrated in FIG. 28 (wherein the container 14L is in the drain position), a similar detent system provides a tactile sensation indicating that the proper position has been reached. To this end, as shown in FIG. 42, the rear plate 422 defines another blind bore 720 about 180° from the blind bore 702. The front plate 424 defines a bore 722 in registry with the blind bore 720. A compression spring 724 is disposed within the bores 720 and 722. A ball 726 is disposed within the bore 722 on top of the compression 724. The ball 726 is retained within the bore 722 by a lip or peened over portion 730 of the front plate 424 around the periphery of the bore 722.

When the rotatable body 430 is rotated to the vertical drain position illustrated in FIG. 28, the bore 716 in the body 430 becomes aligned with the ball 726, and a portion of the ball 726 enters the bore 716 to provide an increased resistance to rotation and a tactile sensation that the drain position has been established.

It may also be desirable in some applications to provide a means for interlocking the operating handle 476 to prevent return of the handle 476 from the rearward position (FIGS. 25–28) to the forward, release position (FIGS. 21–24) except when the body 430 is at a specific rotational orientation or orientations. For example, an appropriate interlock mechanism (not illustrated) can be provided on the transfer device 420 to permit the handle 476 to be rotated from the rearward position to the forward position only when the body 430 is in the load/unload orientation illustrated in FIG. 25. In some applications, it may also be desirable to provide the container closure 20L with indicium corresponding to selected information and to provide a sensing system for sensing the indicium. The sensed information can be used to provide system status indications, alarms, interlocks, or more comprehensive controls, etc. as explained above in detail with respect to indicium and sensing systems illustrated in FIGS. 4–20.

Indicia and sensing systems are schematically illustrated in FIG. 43 as employed in a transfer device 820 which is substantially similar to the transfer device 420 described above with reference to FIGS. 21–42. The transfer device 820 includes a rear plate 822 adapted to be mounted to a vaporizer (e.g., the vaporizer 104B described above with reference to FIG. 21). Mounted to the rear plate 822 is a front plate 824. A body 830 is rotatably mounted to the plates 824 and 822 and is adapted to receive the closure end of an anesthetic container 14M. The transfer device 820 and the container 14M may be substantially similar to the transfer device 420 and container 14L described in detail above with reference to FIGS. 21–42 except that the container 14M has indicia within the container closure and the transfer device 820 has a sensing system at the container closure receiving port region.

As illustrated in FIG. 44, the indicia comprise an electronic microchip 850 and a colored member 852. As illustrated in FIG. 46, the microchip 850 and colored member 852 are mounted in the container closure within the ovate projection 21M.

The sensor system includes an annular antenna 860 mounted on the transfer device 820. The sensor system also includes an optical fiber 864 with the distal end positioned adjacent the container receiving port so as to be in registry with the colored member 852 when the container is properly inserted into the transfer device 820.

The electronic chip 850 may employ conventional surface acoustic wave technology, conventional magnetic datastorage technology, or other suitable, conventional or special information-recording technology.

The color of the indicium 852 can be sensed by the sensing system employing the optical fiber 864. Other technologies may be employed, such as a laser light scannable optical data-storage medium, a laser light scannable bar code record, etc.

Further, mechanical or structural key configurations can be employed.

The various indicia and indicia-sensing systems may be employed in the transfer device 820 to provide signals which can be processed in a filling system in the numerous ways described above in detail with reference to the filling system 102 illustrated in FIG. 4.

It will be readily apparent from the foregoing detailed description of the invention and from the illustrations thereof that numerous variations and modifications may be effected without departing from the true spirit and scope of the novel concepts or principles of this invention.

What is claimed is:

1. A device for receiving a coupling member of a transfer tube connectible to an anesthetic container wherein said coupling member defines at least one anesthetic discharge passage, said coupling member includes a pin for engaging said transfer device, said device comprising:

a body defining (1) a receiving cavity for said coupling member, (2) a fixed cam surface, and (3) at least one fluid transfer passage extending from said receiving cavity through said body;

a rotatable member mounted for rotation on said body and defining a rotatable cam surface; and a clamp member disposed in said body adjacent said receiving cavity and having a first cam follower surface adjacent said fixed cam surface and having a second cam follower surface adjacent said rotatable cam surface whereby rotation of said rotatable member drives said clamp member against said coupling member to clamp said coupling member within said body with communication established between said discharge passage and said transfer passage;

wherein said pin includes at least one indicium thereon, said device further including a sensor for sensing said indicium.

2. The device in accordance with claim 1 in which said sensor includes a system for reading at least one of the following:

an optical data-storage medium; and an electronic data-storage medium.

3. A device for receiving a pierceable closure on an anesthetic container, said device comprising:

a body defining (1) a receiving port for said container closure, (2) a piercing conduit extending into said port, (3) a recess, and (4) at least one fluid transfer passage extending from said piercing conduit through said body;

a rotatable member mounted for rotation on said body and defining a rotatable cam surface; and a clamp member disposed in said body recess adjacent said receiving cavity, said clamp member having a first cam follower surface adjacent said rotatable cam surface and having an inwardly movable cam surface for engaging said container closure whereby rotation of said rotatable member drives said clamp member against said container closure to (1) urge said container closure further into said receiving port wherein said closure is pierced by said piercing conduit and (2) clamp the pierced closure in a fixed position.

4. The device in accordance with claim 3 further including:

a valve member on a valve stem that extends between said transfer passage and said rotatable member and that is guided by said body for reciprocating movement between a first position in which said valve member occludes said transfer passage and a second position in which said valve member opens said transfer passage; and a cam track on said rotatable member engaged with said valve stem for moving said valve stem between said first and second positions when said rotatable member is rotated.

5. The device in accordance with claim 3 for use with said closure wherein at least one indicium is included on said closure, said device further including a sensor for sensing said indicium.

6. The device in accordance with claim 5 in which said sensor includes a system for reading at least one of the following:

an optical data-storage medium; and an electronic microchip data-storage medium.

7. The device in accordance with claim 3 further including a compression spring for biasing said clamp member radially inwardly.

8. A transfer device suitable for mounting on an anesthetic vaporizer for connecting a fluid passage of the vaporizer with an anesthetic container, said transfer device comprising:

a stationary portion adapted to be mounted to said vaporizer at said vaporizer fluid passage, said stationary portion having a fluid passage communicating between said vaporizer fluid passage and at least two locations on a circular arc; and a rotatable body mounted for rotation on said stationary portion, said body defining a receiving region to which said container can be connected and defining a fluid passage communicating between said container and said stationary portion fluid passage when said body is in each of two rotated positions, one of said positions being a fill position and one of said positions being a drain position, said stationary portion has an abutment pin normally biased toward an extended position; and said rotatable body has an engaging pin for engaging said abutment pin when said body is rotated to a predetermined position.

9. A transfer device suitable for mounting on an anesthetic vaporizer for connecting a fluid passage of the vaporizer with an anesthetic container, said transfer device comprising:

a stationary portion adapted to be mounted to said vaporizer at said vaporizer fluid passage, said stationary portion having a fluid passage communicating between said vaporizer fluid passage and at least two locations on a circular arc; and a rotatable body mounted for rotation on said stationary portion, said body defining a receiving region to which said container can be connected and defining a fluid passage communicating between said container and said stationary portion fluid passage when said body is in each of two rotated positions, one of said positions being a fill position and one of said positions being a drain position, said stationary portion has a latch pin normally biased toward an extended position; and said rotatable body has a bore for receiving said latch pin to prevent rotation of said body.

10. A transfer device suitable for mounting on an anesthetic vaporizer for connecting a fluid passage of the vaporizer with an anesthetic container, said transfer device comprising:

a stationary portion adapted to be mounted to said vaporizer at said vaporizer fluid passage, said stationary portion having a fluid passage communicating between said vaporizer fluid passage and at least two locations on a circular arc; and a rotatable body mounted for rotation on said stationary portion, said body defining a receiving region to which said container can be connected and defining a fluid passage communicating between said container and said stationary portion fluid passage when said body is in each of two rotated positions, one of said positions being a fill position and one of said positions being a drain position, said rotatable body has a drive pin movable in said bore for forcing said latch pin out of said bore to permit rotation of said body.

11. A transfer device suitable for mounting on an anesthetic vaporizer for connecting a fluid passage of the vaporizer with an anesthetic container, said transfer device comprising:

a stationary portion adapted to be mounted to said vaporizer at said vaporizer fluid passage, said stationary portion having a fluid passage communicating between said vaporizer fluid passage and at least two locations on circular arc; and a rotatable body mounted for rotation on said stationary portion, said body defining a receiving region to which said container can be connected and defining a fluid passage communicating between said container and said stationary portion fluid passage when said body is in each of two rotated positions, one of said positions being a fill position and one of said positions being a drain position, said stationary portion defines at least one bore containing a ball normally biased to project partially out of said bore; and said rotatable body defines a bore for receiving said projecting portion of said ball in a predetermined rotational position.

12. A transfer device suitable for mounting on an anesthetic vaporizer for connecting a fluid passage of the vaporizer with an anesthetic container, said transfer device comprising:

a stationary portion and a rotatable body mounted for rotation on said stationary portion; said stationary portion and rotatable body defining generally flat, mating faces;

said stationary portion defining a fluid passage communicating between said vaporizer fluid passage and said face of said stationary portion;

said rotatable body defining a fluid passage communicating between said container and said face of said rotatable body;

said fluid passages of said stationary portion and said rotatable body being in communication only in two rotated positions of said rotatable body, said stationary portion has an abutment pin normally biased toward an extended position; and said rotatable body has an engaging pin for engaging said abutment pin when said body is rotated to a predetermined position.

13. A transfer device suitable for mounting on an anesthetic vaporizer for connecting a fluid passage of the vaporizer with an anesthetic container, said transfer device comprising:

a stationary portion and a rotatable body mounted for rotation on said stationary portion; said stationary portion and rotatable body defining generally flat, mating faces;

said stationary portion defining a fluid passage communicating between said vaporizer fluid passage and said face of said stationary portion;

said rotatable body defining a fluid passage communicating between said container and said face of said rotatable body;

said fluid passages of said stationary portion and said rotatable body being in communication only in two rotated positions of said rotatable body, said stationary portion has a latch pin normally biased toward an extended position; and said rotatable body has a bore for receiving said latch pin to prevent rotation of said body.

14. The transfer device in accordance with claim 13 in which said rotatable body has a drive pin movable in said bore for forcing said latch pin out of said bore to permit rotation of said body.

15. A transfer device suitable for mounting on an anesthetic vaporizer for connecting a fluid passage of the vaporizer with an anesthetic container, said transfer device comprising:

a stationary portion and a rotatable body mounted for rotation on said stationary portion; said stationary portion and rotatable body defining generally flat, mating faces;

said stationary portion defining a fluid passage communicating between said vaporizer fluid passage and said face of said stationary portion;

said rotatable body defining a fluid passage communicating between said container and said face of said rotatable body;

said fluid passages of said stationary portion and said rotatable body being in communication only in two rotated positions of said rotatable body, said stationary portion defines at least one bore containing a ball normally biased to project partially out of said bore; and said rotatable body defines a bore for receiving said projecting portion of said ball in a predetermined rotational position.

16. A transfer device suitable for mounting on an anesthetic vaporizer for connecting a fluid passage of the vaporizer with an anesthetic container, said transfer device comprising:

a stationary portion and a rotatable body mounted for rotation on said stationary portion; said stationary portion and rotatable body defining generally flat, mating faces:

said stationary portion defining a fluid passage communicating between said vaporizer fluid passage and said face of said stationary portion;

said rotatable body defining a fluid passage communicating between said container and said face of said rotatable body;

said fluid passages of said stationary portion and said rotatable body being in communication only in two rotated positions of said rotatable body, said transfer device further comprising a sensing system for sensing indicia on said container.

* * * * *